(12) United States Patent
Guldiken et al.

(10) Patent No.: US 9,127,998 B1
(45) Date of Patent: Sep. 8, 2015

(54) ACTIVE ULTRASONIC METHOD OF QUANTIFYING BOLT TIGHTENING AND LOOSENING

(71) Applicants: Rasim Oytun Guldiken, Tampa, FL (US); Jairo Andres Martinez Garcia, Columbus, IN (US)

(72) Inventors: Rasim Oytun Guldiken, Tampa, FL (US); Jairo Andres Martinez Garcia, Columbus, IN (US)

(73) Assignee: University of South Florida, Tampa, FL (US)

( * ) Notice: Subject to any disclaimer, the term of this patent is extended or adjusted under 35 U.S.C. 154(b) by 158 days.

(21) Appl. No.: 14/016,524

(22) Filed: Sep. 3, 2013

Related U.S. Application Data

(60) Provisional application No. 61/696,685, filed on Sep. 4, 2012.

(51) Int. Cl.
*G01L 5/24* (2006.01)
*F16B 31/02* (2006.01)
*G01N 29/07* (2006.01)
*G01L 3/14* (2006.01)

(52) U.S. Cl.
CPC .............. *G01L 5/246* (2013.01); *F16B 31/02* (2013.01); *F16B 2031/022* (2013.01); *G01L 3/1428* (2013.01); *G01L 5/24* (2013.01); *G01N 29/07* (2013.01); *G01N 2291/0422* (2013.01); *G01N 2291/2691* (2013.01)

(58) Field of Classification Search
CPC ... F16B 31/02; F16B 2031/022; G01L 5/246; G01L 5/24; G01L 3/1428; G01N 2291/2691; G01N 2291/0422; G01N 29/07
USPC .............................. 73/761, 627, 620, 861.18
See application file for complete search history.

(56) References Cited

U.S. PATENT DOCUMENTS

| | | | | | |
|---|---|---|---|---|---|
| 5,131,276 | A | * | 7/1992 | Kibblewhite | 73/761 |
| 5,205,176 | A | * | 4/1993 | Kibblewhite | 73/761 |
| 5,220,839 | A | * | 6/1993 | Kibblewhite | 73/761 |
| 5,571,971 | A | * | 11/1996 | Chastel et al. | 73/761 |
| 7,350,420 | B2 | * | 4/2008 | Burmann | 73/761 |
| 2006/0225511 | A1 | * | 10/2006 | Burmann | 73/761 |
| 2014/0360281 | A1 | * | 12/2014 | Helbig et al. | 73/778 |

OTHER PUBLICATIONS

Shah and Hirose, Nonlinear ultrasonic investigation of concrete damaged under uniaxial compression step loading. Journal of Materials in Civil Engineering. 2010. vol. 22: 476-484.

(Continued)

*Primary Examiner* — Lisa Caputo
*Assistant Examiner* — Jonathan Dunlap
(74) *Attorney, Agent, or Firm* — Nilay J. Choksi; Smith & Hopen, P.A.

(57) ABSTRACT

A synthetic phased array surface acoustic wave sensor to quantify bolt tension and a method for determining or estimating the tension in bolts using surface acoustic waves (SAWs). The tension is determined or estimated by using the reflection of SAWs created by the bolt head interference with the underlying surface. Increments in the bolt tension raise the points of interaction between the waves and the bolt head (real area of contact), and hence the position of the reflective boundaries. The variations are estimated using known techniques (e.g., linear synthetic array imaging technique). A singular transducer is actuated from predefined positions to produce an array of signals that are subsequently arranged and added to construct an acoustic image.

15 Claims, 21 Drawing Sheets

(56) References Cited

OTHER PUBLICATIONS

Ledeczi et al., Self-sustaining wireless acoustic emission sensors system for bridge monitoring. Springer-Verlag. Berlin. 2011: 15-39.
Mahmoud et al., Non-destructive ultrasonic evaluation of CFRP-concrete specimens subjected to accelerated aging conditions. NDT&E International. 2010. vol. 43: 635-641.
Amerini and Meo, Structural health monitoring of bolted joints using linear and nonlinear acoustic/ultrasound methods. Structural Health Monitoring. 2011. vol. 10 (No. 6): 659-672.
Automation Creations, "Matweb," [Online]. Available: http://www.matweb.com/search/DataSheet.aspx?MatGUID=3a9cc570fbb24d119f08db22a53e2421&ckck=1. [Accessed Feb. 2012].
Drinkwater and Wilcox. Ultrasonic arrays for non-destructive evaluation: a review. NDT&E International. 2006. vol. 39: 525-541.
Budynas, R.G. and Nisbett, K. Screw, fasteners, and the design of nonpermanent joints. In Shigley's mechanical engineering design; 8th ed.; McGraw-Hill companies,Inc: Burlington, MA, 2006; pp. 396-425.
Holmes et al., Advanced post-processing for scanned ultrasonic arrays: application to defect detection and classification in non-destructive evaluation. Ultrasonics. 2008. vol. 48: 636-642.
Liang et al., Coupled electro-mechanical analysis of adaptative material systems-determination of the actuator power consumption and system energy. Journal of Intelligent Material Systems and Structures. 1994. vol. 5: 12-20.
Silva et al., A structural health monitoring approach based on a PZT network using a tuned wave propagation method. Structures, Structural Dynamics and Materials Conference. Palm Springs, 2009.
Zhu et al., Ultrasonic guided waves for nondestructive evaluation/structural health monitoring of trusses. Measurement science and technology. 2010. vol. 21: 1-12.
Aggelis et al., Assessment of construction joint effect in full-scale concrete beams by acoustic emission activity. Journal of Engineering Mechanics. 2010. vol. 136: 906-912.
Drinkwater et al., A Study of the interaction between ultrasound and a partially contacting solid—solid interface. Proceedings of the Royal Society of London: Series A: Mathematical, Physical and Engineering Sciences. 1996. 452: 2613-2628.
Bazulin, Obtaining flaw images that take the effect of multiple ultrasonic pulse reflections from the boundaries of a test object into account. Russian Journal of Nondestructive Testing. 2010. vol. 46 (No. 10): 735-753.
Esmaeel et al., Computational simulation and experimental verification of a new vibration-based structural health monitoring approach using piezoelectric sensors. Structural Health Monitoring 2011. vol. 11 (No. 2): 237-250.
Mitri et al., Comparison of continuous-wave (CW) and tone-burst (TB) excitation modes in vibro-acoustography: application for nondestructive imaging of flaws. Applied Acoustics. 2009. vol. 70: 333-336.
François et al., Collection mode surface plasmon fibre sensors: A new biosensing platform. Biosensors and Bioelectronics. 2011. vol. 26: 3154-3159.
Gunarathne, Real-time ultrasonic imaging and advancements in non-conventional methods. IEEE International Instrumentation and Measurement Technology Conference. Victoria, Vancouver Island, Cananda. 2008.
Park and Inman. Structural health monitoring using piezoelectric impedance measurements. Philosophical Transaction of the Royal Society. 2007. vol. 365: 373-392.
Goodier. Loosening by vibration of threaded fastenings. Mechanical Engineering. 1945 vol. 67 (No. 12): 798-802.
Uberall. Surface waves in acoustics. Physical acoustics principles and methods. vol. 10. New York. Academic Press, Inc. 2012: 1-15.
Huang et al., Real-time monitoring of clamping force of a bolted joint by use of automatic digital image correlation. Optics & Laser Technology. 2009. vol. 41: 408-414.
Bartoli et al., Use of interwire ultrasonic leakage to quantify loss of prestress in multiwire tendons. Journal of Engineering Mechanics, 2011. vol. 137: 324-333.
Thomenius. Evolution of ultrasound beamformers. IEEE Ultrasonics Symposium. 1996. 1615-1622.
Tanner et al., Structural health monitoring using modular wireless sensors. Journal of Intelligent Material Systems and Structures. 2003. vol. 14: 43-56.
Rose. Dispersion principles. Ultrasonic waves in solid media. New York, Cambridge University Press. 1999: 5-21.
Rose. Surface and subsurface waves. Ultrasonic waves in solid media. New York, Cambridge University Press 1999: 90-99.
Rose. Ultrasonic nondestructive testing principles, analysis and display technology. Ultrasonic Waves in solid media. New York, Cambridge University Press. 1999: 335-357.
Rose, Unbounded isotropic and anisotropic media. Ultrasonic waves in solid media. New York, Cambridge University Press. 1999: 24-37.
Po-Liang and Pei-Ling. Imaging of internal cracks in concrete structures using surface rendering technique. NDT&E International. 2009. vol. 42: 181-187.
Yang and Ume, Thermomechanical reliability study of flip-chip solder bumps: using laser ultrasound technique and finite element methods. Electronic Components and Technology Conference, 2008. 58th: 611-622.
Yu et al., Prediction of fatigue crack growth in steel bridge components using acoustic emission, Journal of Constructional Steel Research. 2011. vol. 67: 1254-1260.
Zhang et al., Defect detection using ultrasonic arrays: the multi-mode total focusing method. NDT&E International. 2010. vol. 43: 123-133.
Zhu and Popovics, Imaging Concrete structures using air-coupled impact-echo. Journal of Engineering Mechanics. 2007. vol. 133 (No. 6): 628-640.
Lee et al., Health monitoring of complex curved structures using an ultrasonic wavefield propagation imaging system. Measurement science and technology. 2007. vol. 18: 3816-3824.
Takeuchi. An Application of Ultrasonic Technique on Measurement of Solid Contact Area. Journal of Japanese Society of Tribologists. 2004. vol. 49: 422-427.
Karaman et al., Optimization of dynamic receive focusing in ultrasound imaging. Acoustical Imaging. 1992. vol. 19: 225-229.
Kendall and Tabor. An ultrasonic study of the area of contact between stationary and sliding surfaces. Proceedings of the Royal Society of London A. 1971. vol. 323: 321-340.
Kim and Hong. Measurement of axial stress using mode-converted ultrasound. NDT&E International. 2009. vol. 42: 164-169.
Królikowski and Szczepek. Phase shift of the reflection coefficient of ultrasonic waves in the study of the contact interface. Wear. 1992. vol. 157: 51-64.
Królikowski and Szczepek. Prediction of contact parameters using ultrasonic method. Wear. 1991. vol. 148: 181-195.
Quifeng et al., Simulation on improving resolution of SAFT. International Conference on Measuring Technology and Mechatronics Automation. Zhangjiajie, China. 2009.
Quifeng et al., Study on improving time-domain resolution on detecting concrete structures. International Conference on Measuring Technology and Mechatronics Automation. Shanghai. 2011.
Satyarnarayan et al., Circumferential higher order guided wave modes for the detection and sizing of cracks and pinholes in pipe support regions. NDT&E International. 2008. vol. 41: 32-43.
Meo et al., Detecting damage in composite material using nonlinear elastic wave spectroscopy methods. Applied Composite Materials. 2008. vol. 15: 115-126.
Schickert et al., Ultrasonic imaging of concrete elements using reconstruction by synthetic aperture technique. Materials in Civil Engineering. 2003. vol. 15 (No. 3): 235-246.
Spies and Rieder. Synthetic aperture focusing of ultrasonic inspection data to enhance the probability of detection of defects in strongly attenuating materials. NDT&E International. 2010. vol. 43: 425-431.
Vogt et al. Synthetic aperture focusing technique for high-resolution imaging of surface structures with high-frequency ultrasound. IEEE International Ultrasonics Symposium Proceedings. Rome. 2009: 1514-1517.

(56) References Cited

OTHER PUBLICATIONS

Garcia, A Novel Ultrasonic Method to Quantify Bolt Tension. University of South Florida. Graduate School Theses and Dissertations. 2012.

Mascarenas et al., A low-power wireless sensing device for remote inspection of bolted joints. Journal of Aerospace Engineering, Part G of the Proceedings of the Institution of Mechanical Engineers. 2009. vol. 223: 565-575.

Milanese et al., Modeling and detection of joint loosening using output-only broad-band vibration data. Structural Health Monitoring. 2008. vol. 7 (No. 4): 309-328.

Portzgen et al., Wave equation-based imaging of mode converted waves in ultrasonic NDI, with suppressed leakage from nonmode converted waves. IEEE Transactions on Ultrasonics, Ferroelectrics and Frequency Control. 2008. vol. 55 (No. 8): 1768-1780.

Park et al., Electro-mechanical impedance-based wireless structural health monitoring using PCA-data compression and k-means clustering algorithms. Journal of Intelligent Materials Systems and Structures. 2008. vol. 19: 509-520.

Wilcox et al., Advanced reflector characterization with ultrasonic phased arrays in NDE applications. IEEE Transactions on Ultrasonics, Ferroelectrics and Frequency Control. 2007. vol. 54(No. 8): 1541-1550.

Pai and Hess. Experimental study of loosening of threaded fasteners due to dynamic shear loads. Journal of Sound and Vibration. 2002. vol. 253 (No. 3): 585-602.

Pai and Hess. Influence of fastener placement on vibration-induced loosening. Journal of Sound and Vibration. 2003. vol. 268: 617-626.

Pau. Estimation of real contact area in a wheel-rail system by means of ultrasonic waves. Tribology International. 2003. vol. 36: 687-690.

Pedinoff et al., Refraction and reflection of surface acoustic waves at boundaries of layered anisotropic substrates: gold on lithium niobate. Journal of Applied Physics. 1971. vol. 42 (No. 8): 3025-3034.

Bhalla and Soh, Structural impedance-based damage diagnosis by piezo-transducer. Journal of Earthquake Engineering and Structural Dynamics. 2003. vol. 32: 1897-1916.

Chaki and Bourse, Guided ultrasonic waves for non-destructive monitoring of the stress levels in prestressed steel strands. 2009. Ultrasonics. vol. 49: 162-171.

Iyer et al., Evaluation of ultrasonic inspection and imaging systems for concrete pipes. Automation in construction. 2012. vol. 22: 149-164.

Sauer et al, Bolts: how to prevent their loosening. Machine Design. 1950. vol. 22: 133-139.

Michaels et al., Frequency-wavenumber domain analysis of guided wavefields. Ultrasonics. 2011. vol. 51: 452-466.

\* cited by examiner

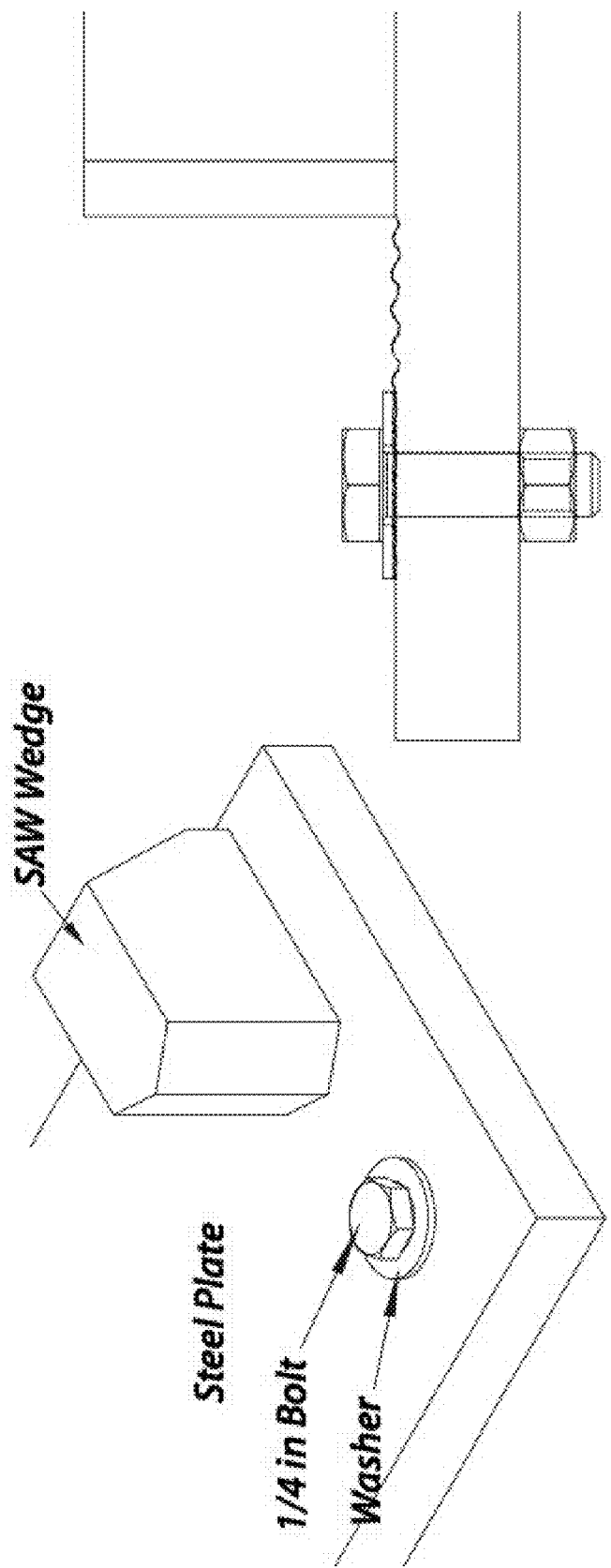

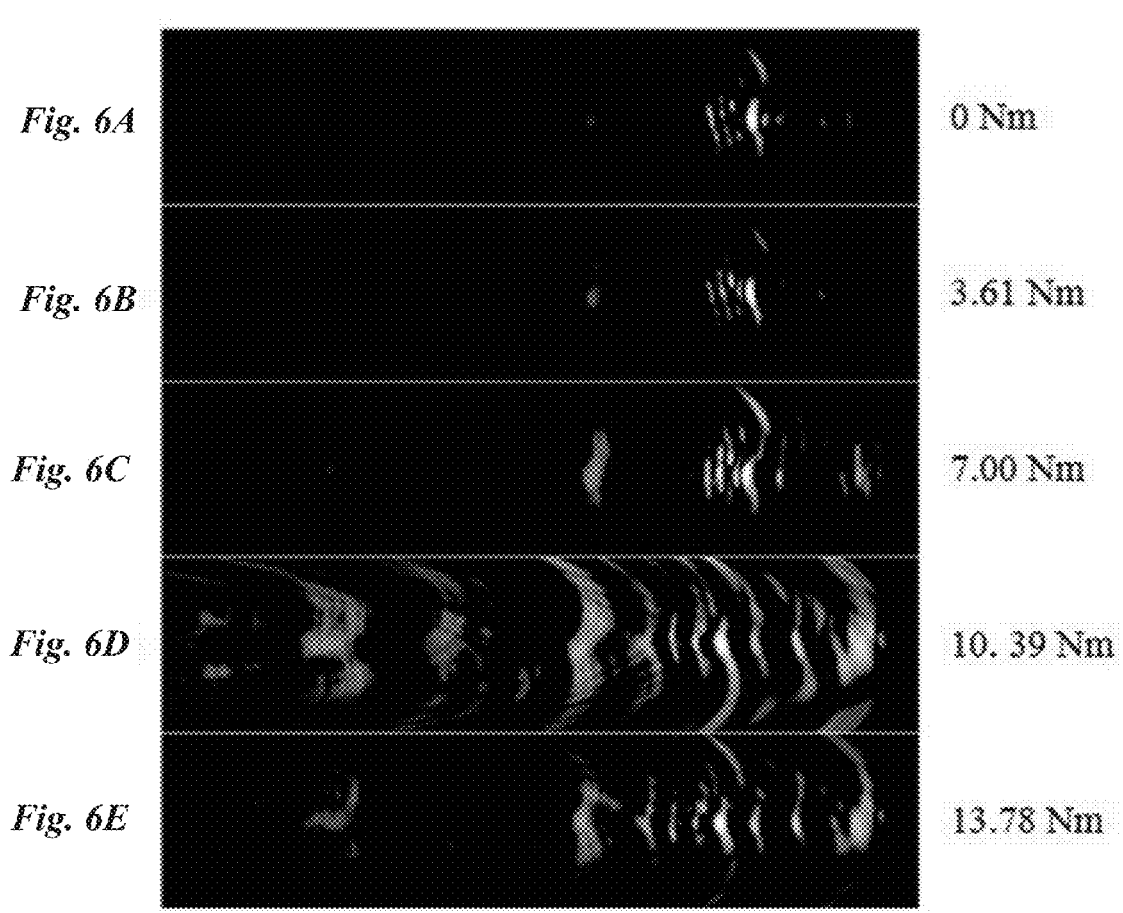
Fig. 6A    0 Nm
Fig. 6B    3.61 Nm
Fig. 6C    7.00 Nm
Fig. 6D    10.39 Nm
Fig. 6E    13.78 Nm

US 9,127,998 B1

ACTIVE ULTRASONIC METHOD OF QUANTIFYING BOLT TIGHTENING AND LOOSENING

CROSS-REFERENCE TO RELATED APPLICATIONS

This nonprovisional application is a continuation of and claims priority to provisional application No. 61/696,685, filed Sep. 4, 2012 by the same inventor, which is incorporated herein by reference.

BACKGROUND OF THE INVENTION

1. Field of the Invention

This invention relates, generally, to monitoring bolt tension. More specifically, it relates to a method of evaluating clamping force using surface acoustic waves.

2. Brief Description of the Prior Art

Threaded fasteners are one of the most versatile methods for assembly of structural components, ranging from small toys to large-scale steel structures such as pipelines, bridges and platforms. The standards of the threaded fasteners employ specific terminology for the parameters that define the general geometry of bolts. FIG. 1A shows the most important parameters of a conventional bolt. The pitch is separation between two contiguous threads. The nominal diameter is the largest diameter of the screw thread. The bolt length is measured from the head to the base. The thread length is the distance from the bolt end to the beginning of the screw thread [1].

Even in an assembly of a single structure, a variety of bolts may be actively used, with ranging sizes and material properties. For example, in steel building structures, two primary types of threaded fasteners are used: critical fasteners and non-critical fasteners. For example, in bridges, large high-strength bolts are used to fix base columns, and small lower-strength bolts are used to support access ladders. High-strength fasteners require careful design and comprehensive care for maintenance. The inspection techniques are used to evaluate clamping force, internal stress and even the crack development in the joint. These techniques are defined by strict standards.

Naturally, not all bolts are critical for the operation of the structure. Fasteners loaded with small forces and present in large quantities do not receive the same treatment as the critical bolts, as they have less importance in structural rigidity. Typical maintenance operations, for example tension measurements, internal stress checking and monitoring of crack development, are not practical or regularly practiced due to cost, time constraints, and the vast quantity of the non-critical fasteners [1]. Although failure of a single non-critical, low-strength fastener likely is not a significant threat to the structure's stability, massive malfunction can cause structural problems, such as insufficient stiffness or excessive vibrations, which may lead to structural failure.

A very common cause of structure failure is the self-loosening of the bolted joints [2-5]. It is explained as a "slip" at the thread-plate and head-plate interfaces [1, 3-7, 14]. The main cause of the "slip" is direct and indirect shear loads applied to the threaded joint [6, 7]. In addition to the shear loads, the preload/tension also tends to loosen the bolt due to the generation of loosening moment related to the helical shape of the thread. Another factor that contributes significantly to the loosening process is the elastic deformation of the fasteners and clamped members; member deformation causes "slip" in the fastener heads and increases the loosening moment in the threads [6].

The health or effectiveness of bolted joints can be defined by one primary parameter: the clamping force (CF). The CF is the force that holds the elements of the joint together. If the CF is too low, separation and bolt fatigue may occur. The CF is too low in loose bolts; low CF indicates the acceleration in the natural loosening process [3], meaning loosened bolts tend to loosen even faster than properly tensioned bolts leading to accelerated bolt loosening as the structure ages [3]. Insufficient CF may further lead to joint separation. In the case of separated bolted joints, aggressive fatigue is induced on the remaining bolts due to the increase tensional stress on the remaining bolts [1, 3]. On the other hand, the CF is too high in excessively tightened bolts; excessive CF may produce damages in the underlying structural members, such as excessive distortion or breakage [3].

The CF is generated by the superposition of the individual tensions of the bolts present in the joint. The bolt tension, also referred to as bolt preload, is the actual force that is stretching the bolt body. The preload is related to the relative stiffness of the bolt and clamped members. Maintaining the appropriate tension in bolts ensures a proper CF and maintains good health of the joint, along with safe operation of the underlying infrastructure. CF is proportional to the bolt tension by the combined stiffness of the clamped members and the fasteners. Tension of all the fasteners in a joint builds up the common force that ensures clamping. Hence, bolt tension of all the fasteners present in a joint is critical for CF [1, 3].

There are two different stages in the operation of bolted joints that require tension control: assembly and regular operation. Geometric characteristics like the stiffness or bolt position usually do not change during the assembly or the regular operation. Thus, accurate tension control is necessary to ensure a correct CF [36]. In the assembly process, the tension is controlled to guarantee a correct preload and therefore the correct CF. On the other hand in the regular operation, the tension is monitored to ensure a safe CF level during the joint life.

Several methods have been studied in order to quantify the health of bolted joints. Typically, the torque control method is applied [1, 4-7, 15]. Other methods are turn-of-nut control [4], direct preload control [4], and stretch control [8]. With torque control, manual, pneumatic or hydraulic torque wrenches are used to apply wide range of torque to the bolt [3]. The inherent dependency of this method on various variables such as friction factor, torsion, bending and plastic deformation of the threads reduce the measurement accuracy of the applied tension to as low as 30% [3, 15].

The turn-of-nut control method has two stages. In the first stage, the bolt is tightened with a conventional torque wrench until it reaches approximately 75% of the material ultimate strength [3]. The second stage involves an additional turn of 1800 after the initial tightening. Every 3600 degree that the bolt rotates increases the bolt length (and hence the tension) by the bolt pitch, so the final turn ensures a tension that creates stresses larger than the bolt material yield point [3]. Tension accuracy of 5% is reported with this methodology. However, this method can only be used for bolts made out of ductile materials with long and well-defined elastic deformation regions [3].

Direct preload control method uses direct estimators of tension, such as strain, stress or deformation. Judiciously positioned strain gauges can measure the strain very precisely leading to tension estimation with an accuracy of as high as 1% [3]. However, as noted, these gauges must be precisely positioned at the bolted joints.

Bolt stretch control is another way to quantify bolt tension. This method employs the transit time of ultrasound measurements along the bolt length to quantify the bolt tension. The main advantage of this methodology is that measurement is independent of friction between the fastener and the clamped plate. Avoiding the friction permits it to be almost as accurate as the instrument used to measure the bolt length change [3]. Additionally, this approach makes it possible to monitor the fastener tension levels only by comparing the new length of the bolt to the value recorded during installation [3]. However, as expected, many older structures with no recorded bolt lengths during installation cannot be evaluated with this method. Also, length variations due to irregular surfaces, uneven machinated processes, temperature changes, plastic deformations and bending displacements introduce significant error to the length estimation.

The common issues with all these frequently used methodologies are their limitation to quantify the bolt tension only during the assembly, measurement capability for a single bolt at a time, relatively high cost, and frequent calibration requirement. However, critical and non-critical bolts should be monitored in real-time; thus, one bolt measurement at a time is a significant limitation for large structures with a high number of bolts.

Response analysis of induced vibrations may be used to characterize the general state of bolted joints. For instance, statistical manipulation can be employed to obtain changes in the vibration signals due to bolt preload variation [8, 16]. Recently, signal processing algorithms based on empirical mode decomposition (EMD) have been used to detect changes in vibration signals produced by impact hammers [17]. This method was also validated empirically and by Finite Element Analysis (FEM). Vibration can be used to monitor common problems, such as stability or resistance in a structure, but identifying the location of the problem becomes a difficult task.

Local approaches, such as monitoring the tension of individual fasteners, can be employed as well [18-21]. The deformations on the fastener were measured by using automatic digital image correlation (ADIC) [18]. Also, piezoelectric sensors were installed in fasteners to sense changes in the electromechanical impedance of the bolts [21]. Guided ultrasonic waves were also used to measure bolt tension. Modulation in Lamb waves due to loosened bolts was used to calculate a joint damage index [19]. Transformation between the wave modes due to stress was exploited by [20] with the purpose of calculating stress levels, tension and CF in the threaded joints. These methodologies often require a direct contact with each bolt to be inspected. Furthermore, a majority of the foregoing methods require either disassembly of the components or data collected during the installation in order to establish the tension levels.

The pitch and catch technique refers to the employment of two different piezoelectric transducers to send and receive guided waves. The waves are sent from the transmitting transducer (T) and acquired by the receiving transducer (R) with information about the material present between them. The waves used in the pitch and catch technique are generally guided waves that can be strongly influenced by small variations in the stiffness or thickness of the material [37]. The pristine condition of the part to be evaluated is taken as baseline for variation of the waves. Modifications in amplitude, dispersion, phase or time of flight are indicatives of changes in the structure of the monitored part. Lamb waves of different modes are used commonly with this technique. Limited space between two transducers is a drawback of this methodology. The waves only provide information from the material in between the transducers. Filtering the acoustic signal may be a necessity for very detailed analysis. For instance, [38] develops a filtering algorithm for diminishing ringing effects, which are common in the imaging generation of concrete structures using pitch and catch techniques.

The principle operation of the pulse-echo method is based in the reflection of acoustic waves. The waves generated in the material are partially reflected by holes, corrosion, dibonding and other defects. The reflected waves carry information that is received by the transducer. The time that it takes for the waves to hit and return to the transducer is called time of flight (TOF). The TOF provides the position of the reflective boundary [33]. The amplitude and frequency of the reflected waves may be used to estimate the size and shape of the defects. Pressure waves are normally employed for through-the-thickness pulse-echo scanning and guided waves, such as Lamb waves or surface acoustic waves, are used for longitudinal monitoring [33]. The principal limitation associated with this method is the difficulty of differentiating boundaries that are close to each other. Proximate defects tend to create reflections that superpose while traveling through the scanned material. Separating the individual effect of each one is critical for a good signal analysis [42]. In some cases this procedure cannot be done correctly, leading to errors in the estimation of size and position of the flaws. Also, the waves employed in the pulse-echo approach generally should be low dispersive in nature, such as bulk waves or surface acoustic waves.

Additionally, the need of previous information about the specific bolt (e.g., its acoustic properties) is a common drawback of the foregoing methodologies. In addition, existing methods cannot measure distantly, disabling simultaneous measurement and prolonging the amount of time and cost needed to evaluate tension in non-critical fasteners, to the point that the non-critical fasteners may not be proactively maintained prior to significant damage caused to the underlying structure.

The prediction of a component's operative life is crucial for its mechanical design. Uncertain loads, ambient conditions, material properties or even misuse are some of the cases that a designer has to overcome in order to predict the life of a specific component. Usually, security factors and redundant designs assure structural integrity even in worst case scenarios. These contingencies generate problems such as increased cost, less efficient designs, or over dimensioned structures. Furthermore, designs that support human lives, like airplanes or civil structures, have additional constrains.

The necessity to predict the operative life of components urged the creation of methods that permit the monitoring of the "health" of structures. The methods that are able to do it without damaging the monitored parts are called non-destructive evaluation (NDE). The principal problem associated with NDE is the necessity of off-line evaluation of components. NDE techniques need very controlled conditions during evaluation processes which normally involve disassembly or service leaving of the monitored component. This kind of monitoring is very common in maintenance programs of any kind of machinery or structure [39].

Structural health monitoring (SHM) overcomes this concrete problem: the evaluation of health is done while the component or structure is in operation. There are two types of SHM according to its monitoring approach. The first kind is called passive SHM, which compares the behavior of the structure while is aging with the original or "brand new"

behavior [39]. The second uses inspection of the components to find actual problems in the structures and is called active SHM [39].

Passive SHM involves monitoring the general state of the components by measuring vibration or monitoring stress levels in critical locations. Static structures can also be monitored [40]. Active SHM involves integrating the NDE into the structure itself, permitting the evaluation and analysis of the structural health whenever needed and without interrupting the normal operation of the component [37-39, 41-49]. Examples include ultrasonic technologies, piezoelectric wafer transducers, etc. However, the known methodologies utilizing passive and active SHM, including those already described, suffer from the same or similar drawbacks as denoted previously.

Accordingly, what is needed is a method of effectively evaluating clamping force, thereby improving the maintenance capability of critical and non-critical fasteners, by utilizing an ultrasonic reflection method that does not require previous information about bolted joint, thus permitting simultaneous in situ quantification of many bolted joints on the same surface. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an effective method of determining bolt tension is now met by a new, useful, and nonobvious invention.

In an embodiment, the current invention is a method of measuring or monitoring tension in a bolt threaded into a bolted joint having a bolt boundary formed from real area of contact between the bolt and the underlying surface. A transducer array element with a predetermined pitch is positioned at a predetermined distance from the joint. An acoustic beam is generated by the transducer array element and is formed of surface acoustic waves. The acoustic beam is directed toward the bolt, such that the surface acoustic waves bounce or reflect off of the bolt boundary at the real area of contact, thus producing a reflected signal. The transducer array element receives the reflected signal in order to determine a distance between the bolt boundary and the transducer array element. This distance is based on time of flight of the reflected signal. Based on this distance, a value of the tension of the joint is generated. The tension and distance have an inverse relationship, such that when distance is higher, tension is lower, and vice versa. The tension is optimal at a saturation point of the real area of contact between the bolt and the underlying surface.

The acoustic beam may be a variable acoustic beam.

The transducer array element may be a linear array. Further, the linear array may be a 1-dimensional transducer array.

The transducer array element may be a phased array.

The transducer array element may include a piezoelectric transducer.

A crystal wedge may be positioned to direct the acoustic beam toward the bolt, where the crystal wedge includes the transducer array element.

The reflected signal may be processed by a beamformer connected to the transducer array element. The reflected signal would be process into an image of the bolt boundary.

The methodology may further include application of a proper time delay to the reflected signal in order to determine the time of flight and location of reflection of the signal.

The step of determining the distance between the bolt boundary and the transducer array element may be performed by generating an ultrasonic image of the joint in order to quantify the real area of contact.

The transducer array element may further generate a plurality of acoustic beams from a plurality of different predefined positions to produce an array of reflected signals. These signals would be used to determine the distance between the bolt boundary and the transducer array element. Further, in order to do that, the signals may be arranged and used to construct a single acoustic image of the bolt boundary.

The transducer array element may be patterned to have a focus point at the bolt.

In a separate embodiment, the current invention is a method of measuring or monitoring tension in a bolt threaded into a bolted joint having a bolt boundary formed from real area of contact between the bolt and the underlying surface. A crystal wedge is positioned at a predetermined distance from the joint and includes a 1-dimensional, linear phased transducer array with a predetermined pitch. The transducer array further includes a piezoelectric transducer. A plurality of variable acoustic beams are generated by the transducer array at different predefined positions and are formed of surface acoustic waves. The acoustic beams are directed toward the bolt, such that the surface acoustic waves bounce or reflect off of the bolt boundary at the real area of contact, thus producing an array of reflected signals that are received by the transducer array. The distance between the bolt boundary and the transducer array can then be determined based on the time of flight of the reflected signals. The time of flight of the reflected signals are generated by applying a proper time delay to the reflected signals. This application of time delay further generates locations of reflection of the reflected signals. The distance is determined by a beamformer connected to the transducer array, where the beamformer processes the reflected signals to generate an ultrasonic image of the joint and bolt boundary in order to quantify the real area of contact. Based on the distance between the bolt boundary and the transducer array, a value of the tension of the bolt/joint can be generated. The tension and distance have an inverse relationship, such that when distance is higher, tension is lower, and vice versa. The tension is optimal at a saturation point of the real area of contact between the bolt and the underlying surface.

In a separate embodiment, the current invention is a system for measuring or monitoring tension in a bolt threaded into a bolted joint having a bolt boundary formed from real area of contact between the bolt and the underlying surface. The system includes a transducer array and a beamformer connected to the transducer array. The transducer array has a predetermined pitch and is positioned at a predetermined distance from the joint. The transducer array generates and directs an acoustic beam toward the bolt. The acoustic beam is formed of surface acoustic waves that reflect off of the bolt boundary at the real area of contact, thus producing a reflected signal that is received by the transducer array. The beamformer processes the reflected signal and generates an acoustic image of the joint, thus permitting a determination of the distance between the bolt boundary and the transducer array. The tension and distance have an inverse relationship, such that when distance is higher, tension is lower, and vice versa. The tension is optimal at a saturation point of the real area of contact between the bolt and the underlying surface.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 2A is a perspective view of a wedge used to generate SAWs in a metal plate towards a previously tensioned bolt, according to an embodiment of the current invention.

FIG. 2B is a side view of the system of FIG. 2A.

FIG. 6A is an image of a steel plate generated at 15 dB with the SAW reflection from a ¼ in bolt with a stainless steel washer at 0 Nm of applied torque.

FIG. 6B is an image of a steel plate generated at 15 dB with the SAW reflection from a ¼ in bolt with a stainless steel washer at 3.61 Nm of applied torque.

FIG. 6C is an image of a steel plate generated at 15 dB with the SAW reflection from a ¼ in bolt with a stainless steel washer at 7.00 Nm of applied torque.

FIG. 6D is an image of a steel plate generated at 15 dB with the SAW reflection from a ¼ in bolt with a stainless steel washer at 10.39 Nm of applied torque.

FIG. 6E is an image of a steel plate generated at 15 dB with the SAW reflection from a ¼ in bolt with a stainless steel washer at 13.78 Nm of applied torque.

DETAILED DESCRIPTION OF THE PREFERRED EMBODIMENT

Figure 1A:
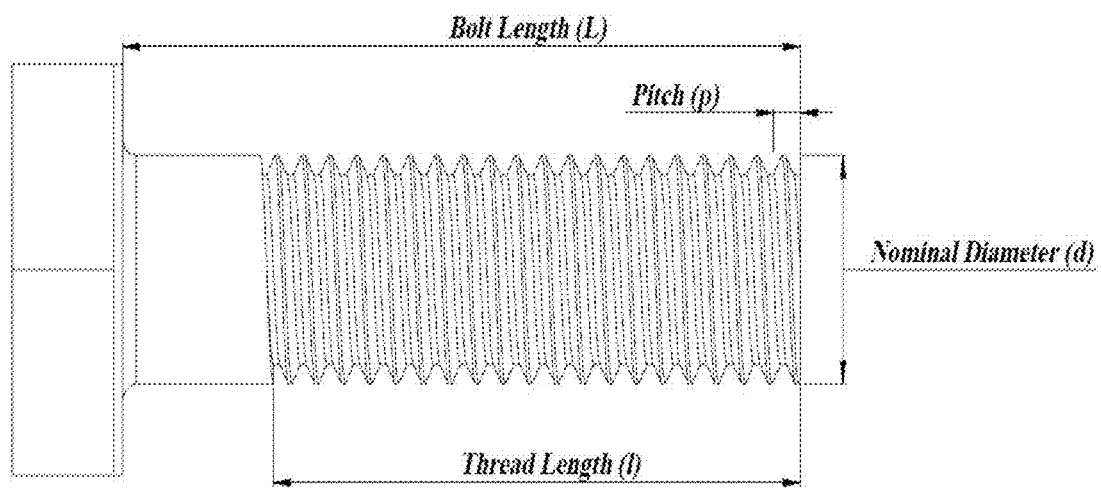
FIG. 1A depicts the geometrical characteristics of a standard bolt.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

The interaction of various acoustic wave modes with the boundaries of rough surfaces has been widely studied [24-29]. However, in certain embodiments, the novel methodology determines the reflection of surface acoustic waves (SAWs) created by the bolt head interference in order to quantify bolt tension without contacting the bolt. Surface acoustic waves are used to estimate changes in the area of real contact created in-between the bolt head and the clamped elements. SAWs interact with solid elements in the surface of the propagation medium [15]. The interaction (for example with the bolted joint) takes place at the points where the propagation surface and the external body are directly in contact with each other, referred as points of real contact, which will become more clear as this specification continues.

The advantages of SAWs as compared to other acoustic modes are that they propagate over long distances with little amplitude loss enabling large area inspection with minimal number of sensors, thus reducing the cost and complexity [23]. Secondly, SAWs are capable of propagating through surfaces of curves and to inaccessible locations, simplifying the design. Also, SAWs are sensitive to many different kinds of flaws. Here, RAC, which grows with increased bolt tension, is quantified by its acoustic signature response to SAWs. Real areas of contact (RAC) formed between the bolt head and the clamped elements were imaged using a synthetic phase array. SAWs are generated and sensed by known bulk piezoelectric transducers connected to a custom-designed ultrasonic wedge.

The velocity, attenuation, and imaging of SAWs in steel 1018 is calculated and shown in [9], which is incorporated herein by reference in its entirety. A series of SAW reflections were acquired at different positions to help measure the intensity changes of the waves while they propagated through the plate. The results confirmed the exponential behavior of the wave attenuation and deliver the attenuation coefficient that can be used with certain embodiments of the current methodology.

In an embodiment, the current invention includes a method for distant detection of tension/preload between the bolt and the surface. Acoustic beam is generated, for example by utilizing a linear transducer array, using SAWs transmitted by array elements. The bolt boundary reflects SAWs; array elements receive the echo signals that are processed in the beamformer to generate the image of bolt boundary. The distance between the bolt boundary and the array is measured using the processed image. The distance is proportional to the tightening pressure between the bolt and the surface. The measured pressure value enables strong estimation about the health of the bolted joint.

Figure 1B:
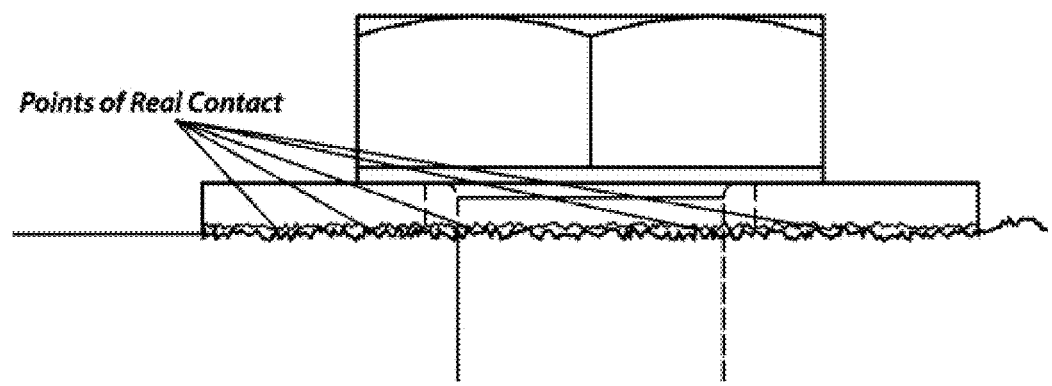
FIG. 1B depicts the real contact surface of a clamped plate and a washer.

The pressure between a bolt and its corresponding surface is a function of the contact area. In an embodiment, the current method measures the contact area, but the contact area is not the apparent area that determines RAC [10-12]. The RAC is the sum of areas of individual contacted micro-scaled surfaces between the joint members as illustrated in FIG. 1B. The points of real contact correspond to the tips of the surface peaks in both materials making direct contact with each other and this represent only a small portion of the entire apparent area of contact. The interaction between the peak tips illustrates the formation of the friction force due to molecular interaction and mechanical resistance. At the micro scale level, adhesive forces due to electromechanical molecule interaction result in significant friction force component. Vander Waal interaction, ionic, covalent and metallic links between the molecules of both materials generate another opposition force to the movement.

In addition to the molecular forces, the resistance produced by plastic and elastic deformations of the peak tips, completes the friction force ($F_T$) [12]. The independency of the friction from the geometrical area is a natural cause of the difference between the real and the apparent area of contact [12]. Furthermore, several experiments have shown that the real area of friction is proportional to the normal force when either elastic or plastic deformations are present [10-12]. The presence of only elastic deformations of the peaks implies the existence of a constant mean micro contact area. Consequently the real area of contact is proportional to Torque (T) and CF in bolted joints, as seen in Equation (1):

$$T \propto F_T \text{RAC} \propto F_T \Rightarrow \text{RAC} \propto T \tag{1}$$

Figure 1C:
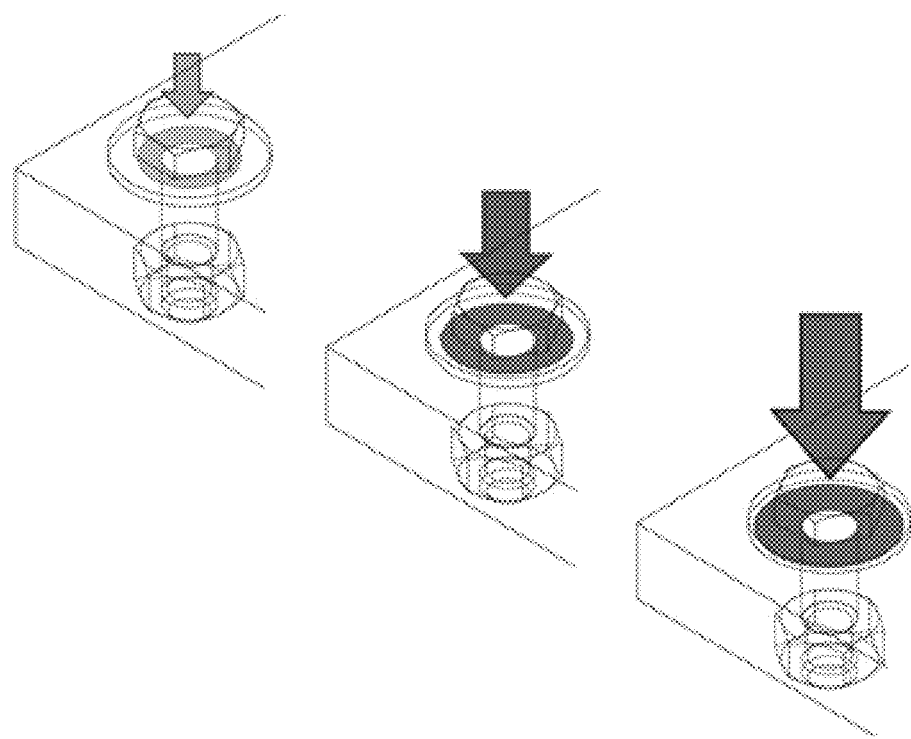
FIG. 1C is a schematic representation of the changes in the RAC due to the incremental increase of bolt tension.

In an embodiment of the current invention, SAWs are utilized to detect the RAC. SAW, similar to other types of ultrasonic waves, suffers attenuation, reflection and refraction due to interactions with entities in contact to the propagation surface. Hence, SAW can be used for imaging purposes. A phased array that produces SAW beams should be used to obtain the image of the bolt boundary. The width of bolt boundary is proportional to the RAC (FIG. 1C). The number and size of points of contacts increase with increasing tension in the bolt [12, 30].

FIG. 1C is a schematic representation of RAC growth due to increasing bolt tension. As can be observed from FIG. 1C, as the tension increases (signified by the arrows), the RAC between the plate and the washer increases as well (signified by the "donuts"). The RAC is different from the apparent areas of contact, but at high-tension levels, the differences between the RAC and the apparent areas of contact become minimized [12]. The saturation of the RAC at a specific preload level establishes the maximum tension level that should be applied to the bolt for optimal and safe operation. The way in which the RAC grows aids in the estimation of the bolt tension.

As illustrated in FIG. 1C, the RAC grows from the center of the washer towards the washer perimeter. This behavior can be explained by analyzing the way the tension is applied to the bolt head. The preload transforms into a pulling force exerted to the head center. The surface peaks closer to the center are then affected more than the ones in the perimeter. Thus, the expansion of the RAC can be predicted as propagating radially outward.

In an embodiment, SAWs are transmitted to the area of interest, and the echo is received using a 1-dimensional (1-D) linear transducer array. Proper delays are applied to each received signal to get the B-Scan image of the interested area. The delays ($\tau$) are calculated by dividing the distance between array element and imaging point by the ultrasound velocity as seen in Equation (2) where c is ultrasound velocity, ($x_p$, $z_p$) is the coordinate of the point in imaging area, and ($x_i$, 0) is the coordinate of array element. Each image line is obtained by shifting each received signal according to calculated delay and by summing the shifted signals. Equation (3) shows the expression to find each image line: I(t). $A_i$ is the aperture function applied to each receive and transmit element, $s_{i,j}$ is the received signal corresponding to $i^{th}$ transmit and $j^{th}$ receive element, and $\tau_i$ refers to transmit and receive delays [13].

$$\tau_i = \frac{1}{c}((x_i - x_p) + z_p)^{1/2} \tag{2}$$

$$I(t) = \sum_{i=1}^{N} A_{tx,i} \sum_{j=1}^{N} A_{rx,j} s_{i,j}(t - \tau_{tx,i} - \tau_{rx,j}) \tag{3}$$

In FIGS. 2A and 2B, a schematic presentation of an exemplary method according to the present invention can be observed. A crystal wedge is used to generate SAW in a metal plate towards a previously tensioned ¼ inch bolt. The SAW can interact with elements in the surface of the propagation material (PM) at the RAC. The existence of discrete points of contact between two rough surfaces means that incident SAWs propagating below a solid object will interact with an undefined number solid-solid and solid-gas (air) boundaries.

Figure 2C:
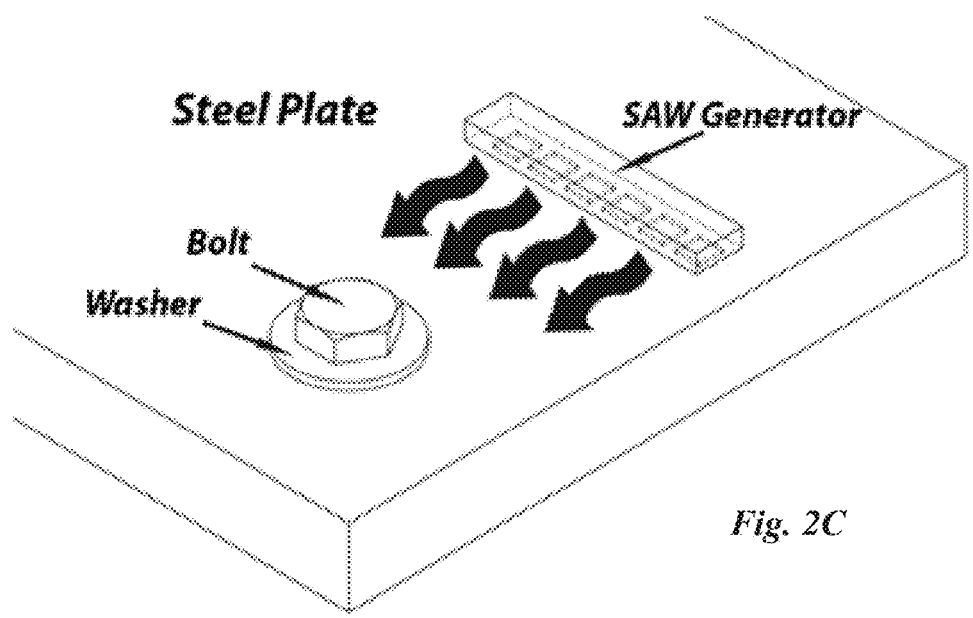
FIG. 2C is a perspective view of a wedge used to generate SAWs in a metal plate towards a previously tensioned bolt, according to an embodiment of the current invention. The arrows represent the direction of the SAWs.

As can be seen in FIG. 2C, a SAW generator can receive the echo signals as well. An N×1 beamformer is fed using the received signals in order to generate B-scan image around the bolt. The distance between the hole and the array is determined using this image. The maximum distance is measured if there is no bolt. In case of the maximum applied torque, the boundary will be closer in an amount equal to width of the washer or the bolt.

Waves created by a SAW generator are directed towards a bolted joint. As the tension at the bolt is increased, the position of the reflective boundary is expected to move from the edge of the joint towards the outer washer perimeter, as presented in FIG. 2D. The increase in the bolt tension results in a proportional increase in the RAC, represented by the circles in FIG. 2D. The arrows represent the incident waves pointing to the left and the reflected waves pointing to the right. The reflected arrows represent the SAW reflections from the plate hole and the RAC corresponding to tension states of low, medium and high intensity, respectively from left to right.

Figure 2D:
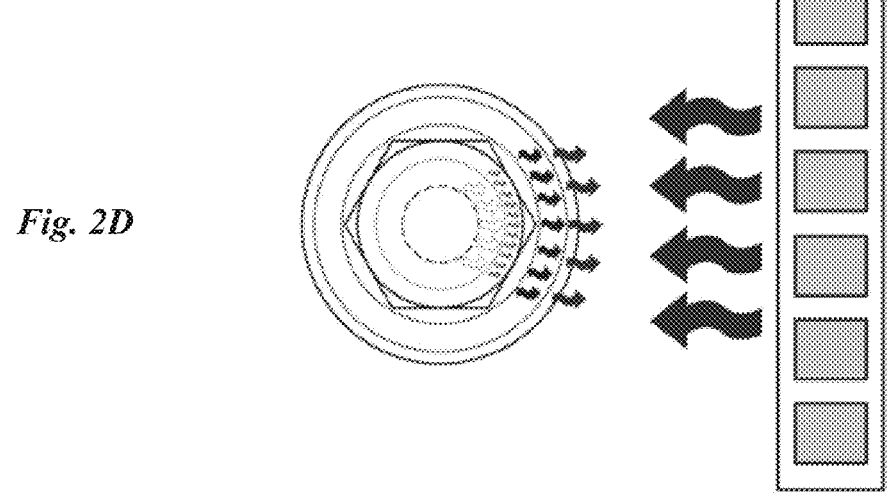
FIG. 2D is a top view of the system of FIG. 2C. The four (4) levels of arrows pointing to the right are a representation of SAW reflection from four (4) different boundaries. The four (4) levels of arrows represent, respectively from left to right, no load, low load, medium load, and high load. The arrows on the right side pointing toward the left represent the incoming SAWs.

The change in position of the acoustic wall denotes a change in the tension applied to the bolt head. An acoustic wall is a series of points where free movement of the waves is constrained, for example the contact points of two solid objects. Material discontinuities, holes and object edges also behave as acoustic walls. In FIG. 2D, a schematic representation of the SAW reflection from different acoustics barriers is illustrated. The RAC find its minimum value when the bolt has no tension, which would show the main reflections coming from the plate hole (left-most arrows pointing to the right). As the preload is increased and the RAC grows, the main reflections move from the hole boundary and get closer to the washer perimeter (right-most arrows pointing to the right). FIG. 2D illustrates the reflection of four (4) different states: no load, low load, medium load, and high load, in the order from left to right with the arrows pointing to the right. The changes in position of the acoustic wall are represented by a delay in the received wave, which means that every preload value has a related wall position represented by a specific time of flight (TOF) of the reflected waves. A relationship TOF vs. bolt tension can be generated.

Figure 3A:
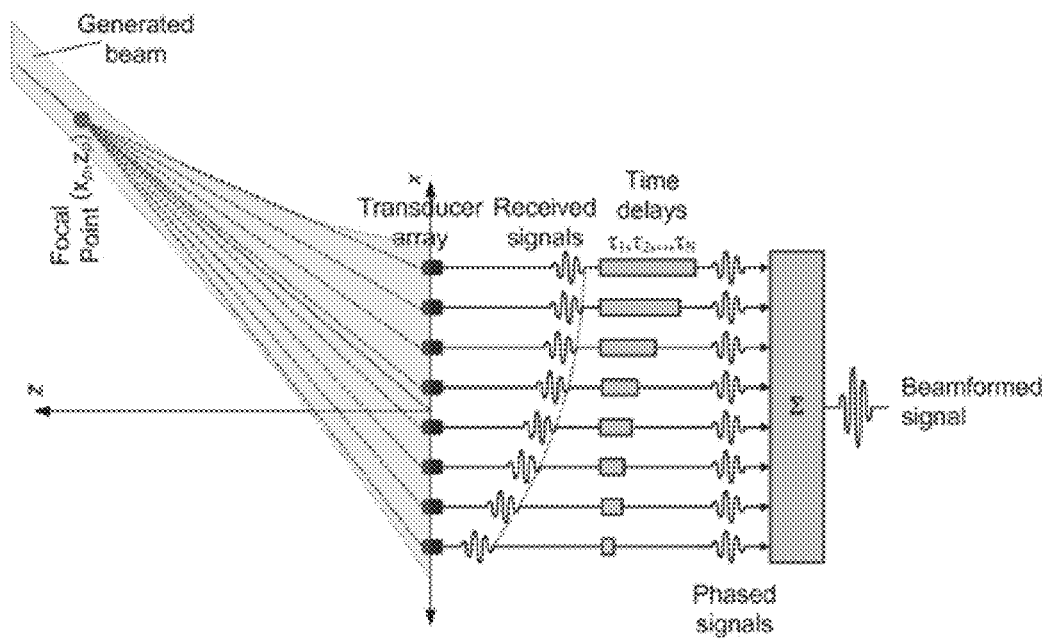
FIG. 3A depicts construction of a beamformed signal by scanning the interested area using a transducer array.
Figure 3B:
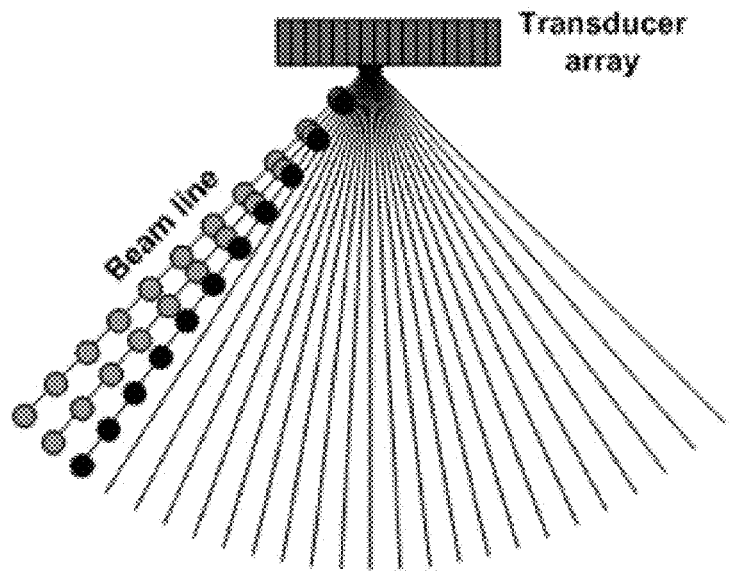
FIG. 3B depicts the scanning of FIG. 3A by constructing successive beamlines.

The method employs a phased array to obtain the B-scan ultrasonic image of the bolted joint in order to quantify the RAC, which is proportional to tension level in the bolted joint. Ultrasonic image of the bolt assembly is obtained by generating SAW pulses and receiving the echoes using the array elements. Each beam line in the image is constructed by summing the beamformed signals. The method of constructing the images is illustrated in FIGS. 3A-3B where the $\tau_1$ to $\tau_N$ represent the proper delays and the output is the beamformed signal corresponding to focal point. The delay profile for each focal point in the beam line is calculated using Equation (4):

$$\tau_i = \frac{1}{c}[R_p - ((x_i - x_p) + z_p)^{1/2}] \quad (4)$$

where c is the SAW velocity, $(x_i, 0)$ is the coordinate of array element, $(x_p, z_p)$ is the coordinates of the focal point on the beam line and $R_p$ is the distance between the array center and focal point.

SAW velocity (e.g., ~2900 m/s) was calculated by the Rayleigh wave equation [27], and verified by ultrasonic delay time (pulse-receive) experiments performed on the 1018 steel plate by using two transducers. The delay that is calculated for each transducer element basically eliminates the differences of flight time that is the travel duration from focal point to the each array element. The sum of properly delayed signals results in an in-phase sum called beamformed signal. The mathematical expression to determine the beamformed signal is given in Equation (5). Here, $A_i$ is the aperture function applied to each receive and transmit element, $s_{i,j}$ is the received signal corresponding to ith transmit and jth receive element, $\tau_1$ is refer to transmit and receive delays [13]. Dynamic focusing is employed in receive mode; thus, each beam line is obtained by summing the beamformed signals obtained by focusing to each radial point [32]. The combined beamlines form the image of the interested area (illustrated in FIG. 3B).

$$B(t) = \sum_{i=1}^{N} A_{tx,i} \sum_{j=1}^{N} A_{rx,j} s_{i,j}\left(t - \tau_{tx,i} - \tau_{rx,j} + \frac{2R_p}{c}\right) \quad (5)$$

The location of bolt boundary is obtained using the ultrasonic image by measuring the distance between the boundary and the array center since it is proportional to the RAC. The distance is an important parameter to determine the health of the bolted joint.

Significant advantages of this methodology is its capability to assess bolt tension without any contact to bolt enabling measurement at inaccessible locations, multiple bolt measurement capability at a time, not requiring data collection during the installation and no calibration requirement.

EXAMPLES

The following examples are intended to exemplify particular embodiments of the current invention but are not intended to limit the scope of the current invention in any way.

Bolt tension is measured by SAWs. A linear transducer array is employed for creating a variable acoustic beam, thus enabling local or remote inspection of bolted joints. Additionally, if a linear phased array is utilized, the direction variability of the acoustic beam enables simultaneous monitoring of a higher number of bolted joints.

The tension is estimated using the reflection of SAWs created by the bolt head interference. Increments in the bolt tension rise the points of interaction between the waves and the bolt head (real area of contact) and therefore the position of reflective boundaries. The variations are estimated using the "conventional linear synthetic array" imaging technique. A singular transducer is actuated from predefined positions in order to produce an array of signals that are subsequently arranged and added to construct an acoustic image.

Examples are presented herein to exemplify the tension estimation of a ¼" grade 8 bolt, a ¼" stainless steel bolt, and a ½" stainless steel bolt. The tension is not directly measured nor applied to the bolt; rather, controlled torque is used to generate the changes in the RAC. The torque and bolt tension produce equivalent effects in the RAC. Three (3) types of figures summarize the experimental results: (1) a 2-D image of the reflective objects in the scanned surface, (2) a 1-D averaged plot of the images, and (3) a plot of the torque applied versus position of the reflective boundary.

The 2-D image of the reflective objects in the scanned surface is a representation of the signals received by the transducer. The lighter colors represent reflection with higher intensity while darker with lower intensity. The images allow visualization of the position where the highest reflections take place. In the examples, the reconstructed images illustrate a clear trend in the position of the reflective boundary when the applied torque is changed. In all cases, the torque increments increase the RAC and therefore the position of the reflective boundary. As expected, the RAC grew from the bolt head center to the perimeter, which causes an effect of apparent movement of the boundary. The reflections of the SAWs only interact with the outer boundary of the RAC, and as it grows, the position in which the interaction takes place moves towards the array location.

The 1-D average plot is a simplification of the 2-D image. Taking the average of lateral dimension of the 2-D image the graph is created. The 1-D plot permits establishing the exact position of the maximum intensity point of the 2-D image. The position of this point is used to estimate the actual distance change of the reflective boundary. In each example, this plot illustrates the same trend found in the 2-D image, i.e., that the boundary moves towards the array as the torque is increased. The averaged 1-D plot also permits comparison of the torque level to the actual boundary position, which is a manner of measuring the bolt tension using embodiments of the current methodology.

The final outcome are plots of the boundary position versus the torque applied to the bolt. The graphs illustrate the actual change in position produced by the variation in the torque. The test performed to the ½ in bolt presents an almost linear variation of the boundary position with the torque. In the in grade 8 bolt, the results indicate two regions within the graph. The first region presents a non-linear behavior, while the second one is a saturation region. The saturation region (presented at the highest torque values) is characterized by slight changes in the boundary position due to torque increments.

Example 1

Tension Evaluation of a ¼ inch Grade 8 Bolt

An embodiment of the proposed method was investigated to test higher tension levels. Grade 8 bolts have yield strength almost three (3) times higher than stainless steel bolts [50], which are used in Examples 2 and 3. Additionally, a stainless steel washer is fixed to the bolt in order to increase the expansion capability of the RAC.

A 5-MHz, 50-array elements synthetic array was utilized. The pitch was chosen as 0.0254 cm in order to sample the beamspace precisely. In all, an almost linear "preload-boundary distance" relation was observed, but as expected, the change in the preload slightly affected the boundary distance in too low and too high preload regions. In other words, two saturation regions and a linear region were clearly observed. SAW beams were used to measure the pressure between the bolt and the surface. If a phased array is used, the electronic steering of the array would enable simultaneous health measurements of many bolted joints on the same surface. The distant pressure measurement sensor could be integrated into a data acquisition system to track the health of the joints over time.

Experimental Setup

In this example, a synthetic aperture technique was used instead of phased array imaging. The synthetic phased array reduces the complexity of the phased array by using only one (1) element in transmitter-receiver mode. Two approaches can be used with this method: conventional synthetic aperture or synthetic phased array. In the conventional synthetic aperture, one (1) transducer is mechanically manipulated in order to create the desired array. The transducer's transmitter and receiver are in different positions. The synthetic phased array use a real array of transducer, but in a particular time only one (1) transducer acts as transmitter and receiver. The other elements act as receivers only, thus permitting the increment of the image quality while significantly reducing the system complexity [51].

Figure 3C:
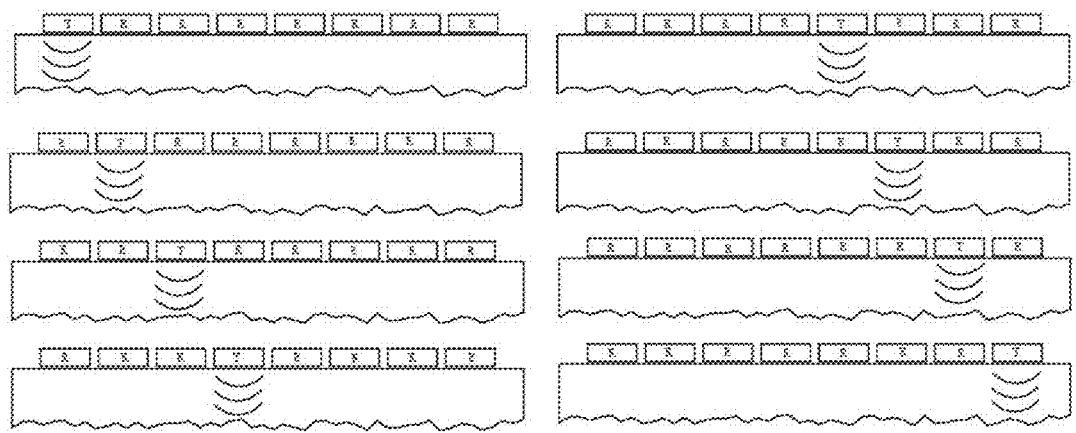
FIG. 3C depicts a schematic operation procedure of the synthetic phased array.

Contrary to the phased array approach, in the synthetic array methodology, the acoustic beam is not focused on a single point or direction as in FIG. 3A. The beam is produced by a single element and therefore the beam focus is the natural focus of the transducer as in FIG. 3B. The beam is expected to generate waves in all the scanned area, and the reflection should be detected by the remaining array elements. It is shown in FIG. 3C that the transmitter-receiver mode is alternated within the elements, hence a complete scan only finishes when all the elements have acted as transmitter and receiver [51, 52].

The image reconstruction is similar to the phased array approach. The reflection signals are focused with time delays. In this case the reconstructed signal is a 2-D sector image, so the transducer creates an image of the scanned area when a particular transducer is actuated. The images are then added in order to form the final picture. The signal can be reconstructed following the following formulation [53]:

$$r(x', y') = \sum_{j=1}^{N} w_j s_j\left(t_o + \frac{2}{c}\sqrt{(x' - x_j)^2 + y'^2}\right) \quad (6)$$

where $w_j$ is a weighting parameter, mostly used for attenuation adjustments, $s_j(t)$ is the actual signal received by the $j^{th}$ transducer, t is the time needed nullify the effects of the electronic devices, C is the sound speed velocity of the scanned material, x is the transversal position of the $j^{th}$ array element, N is the total number of transducers and finally $r_{x,y}$ is reconstructed value of the pixel with coordinates (x',y'). The initial signal s(t) may be interpolated for increasing the number of pixels in the image and therefore the image resolution.

Due to the inherent advantages of the synthetic aperture focusing, many studies have been performed in order to improve its efficiency and its applicability in strongly attenuative materials. In reference [54, 55, 56] some modified algorithms based in this methodology have shown improvement in the image quality in very difficult materials such as concrete and ferritic-austenitic stainless steel.

Despite some of the noted advantages of using synthetic phased array imaging, phased array imaging may be utilized with the current invention as well, along with other suitable acoustic imaging systems (i.e., having appropriate axial resolution, lateral resolution, contrast resolution, and signal to noise ratio).

Figure 4:
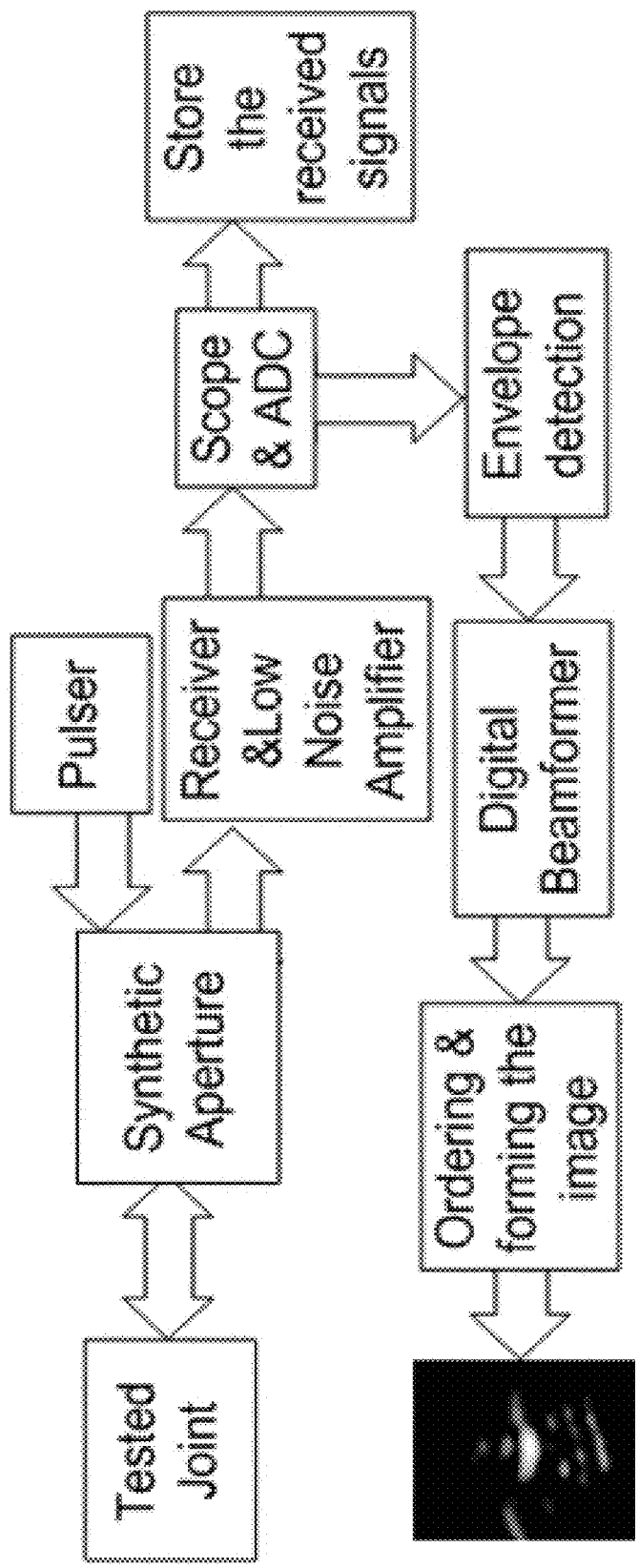
FIG. 4 is a block diagram of the experimental setup of Example 1.
Figure 5A:
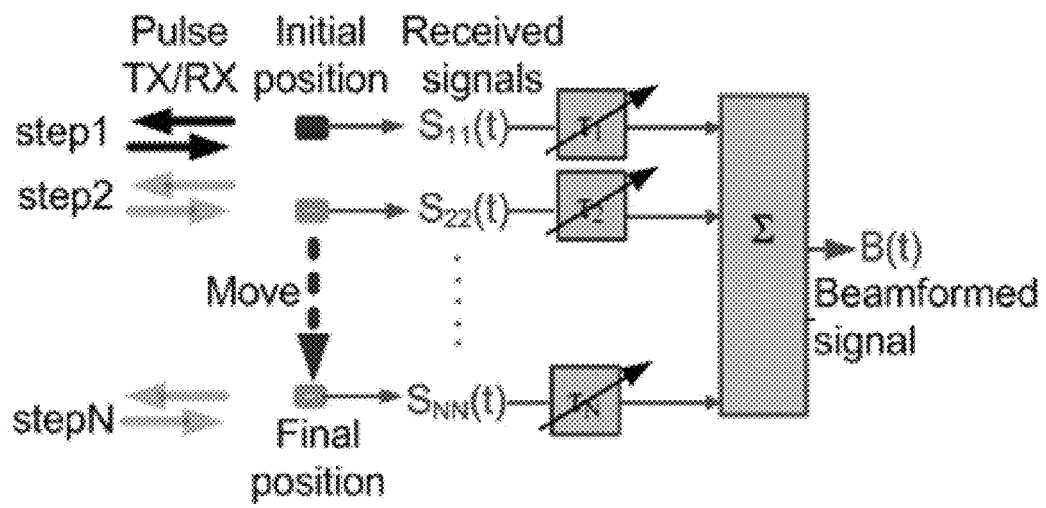
FIG. 5A is an illustration of synthetic aperture imaging.
Figure 5B:
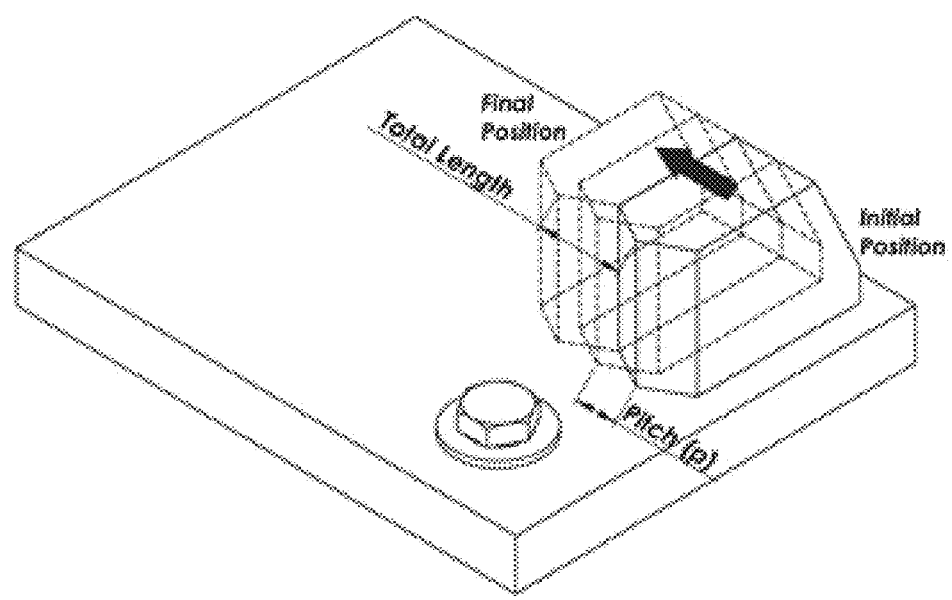
FIG. 5B is an illustration of the experimental implementation of Example 1.

The experimental setup is illustrated by the block diagram seen in FIG. 4. The SAW is generated using a 5-MHz transducer with a 70 degree wedge. The transducer is stepped linearly to form a synthetic 1-D array as illustrated in FIG. 5B.

Fifty (50) steps were used; thus, the number of elements in the linear array was fifty (50). The pitch was chosen as 0.0254 cm in order to sample the beamspace precisely. Thus, the total length of the array was 1.27 cm. The distance between array and the hole boundary was 2.8 cm.

The tested joint was made by a 1018 steel plate of 12.7 mm thickness, a 6.35 mm grade 8 bolt, and a stainless steel washer with 1.5 cm of internal width and 19 mm of external diameter. The suitability of the 1018 steel plate in these examples was determined in [9]. The SAW velocity in the plate was 2952 m/s. Five (5) different torque values were used and the boundary distance measured. This creates create an accurate trend of the TOF with respect to torque changes. The maximum torque for the used bolt was 13.78 Nm with 3.61 Nm increments, so the following torque values were selected: 0 Nm (no bolt), 3.61 Nm, 7 Nm, 10.39 Nm, and 13.78 Nm. The joint was lubricated with general purpose oil in order to facilitate the tightening process, so a reduction in 10% in the friction factor is required to assure no bolt rupture. The configuration of components of this Example is presented in Table 1.

TABLE 1

Parameters employed in Example 1.

| | |
|---|---|
| Pulse generator damping | 50 Ω |
| Pulse generator PRF | 200 Hz |
| Amplification | 45 dB |
| Pulse generator LPF (1 MHz) | ON |
| Pulse generator HPF (10 MHz) | ON |
| SAW velocity | 2590 m/s |
| Transducer frequency | 5 MHz |
| Transducer diameter | 0.5 in |
| Array pitch (in) | 0.01 in |
| Number of elements | 50 |
| Target distance | 2.7 in |
| Bolt diameter | 0.25 in |
| Bolt yield strength | 130 ksi |
| Friction factor | 0.18 |
| Tensile stress area | 20.516 mm² |
| Maximum torque | 17.86 Nm |
| Torque increments | 3.61 Nm |

The wideband excitation pulses were generated, and the echoes were received and amplified by a pulsar-receiver or pulse generator (Olympus 5072PR, Olympus NDT Inc., Waltham, Mass.). The received signals were displayed/digitized by an oscilloscope (Tektronix TDS 2024B, Textronix Inc., Beaverton, Oreg.). The digitized signals were stored in a computer and the image generated using a custom-designed MATLAB code.

The ultrasound images were obtained using a synthetic array imaging system, rather than a phased array system. Synthetic array imaging was chosen due to the simplified beamformer structure, although it may degrade the image quality by lowering the signal-to-noise ratio (SNR).

Synthetic phased array was formed by a single angle beam transducer actuated from several positions within a linear array. The wideband SAW pulse is transmitted, and the echo is received in each movement step (FIG. 5A). Consequently, N-element linear array is synthetically formed using a single moving transducer. It should be noted that synthetic array imaging cannot achieve all of the transmit-receive (TX/RX) combinations; the transmitted array element should receive the echo. The missing TX/RX combinations result in decreased SNR as compared to phased imaging modality. However, the major advantage of synthetic phased array modality is a significantly simplified beamformer since the total number of TX/RX combinations is decreased [13, 32-35].

$$B(t) = \sum_{i=1}^{N} A_{rx,i} A_{tx,i} s_{i,i}\left(t - 2\tau_i + \frac{2R_p}{c}\right) \quad (7)$$

A 5 MHz bulk piezoelectric transducer (C541-SM, Olympus NDT Inc., Waltham, Mass.) with circular aperture of 12.7 mm (½ in) was used and attached to an ultrasonic wedge that is specifically designed for converting bulk pressure wave (P-wave) into SAWs in steel (ABWML-5T, Olympus NDT Inc., Waltham, Mass. USA). Ultrasonic couplant (Soundsafe, Sonotech Inc., Glenview, Ill., USA) was used at the surfaces between the wedge and the transducer and between the wedge and the test piece to facilitate the transmission of ultrasonic energy. The transducer-wedge system is linearly moved to realize synthetic array. The position control of the angle beam transducer (transducer-wedge attachment) was achieved through a manual translator stage (PT3, Thorlabs Inc., Newton, N.J., USA) consisting of micrometers with resolution of 25 μm and maximum displacement range of 25.4 mm. The transducer and the wedge were adapted to the translator stage by custom designed aluminum adaptors. In FIG. 5B, two important features of the synthetic linear array are illustrated: array pitch (p) and total array length. The array pitch was selected as 250 μm corresponding to less than half the wavelength. With this selection criterion, sufficient lateral resolution was achieved and formation of side lobes in the acoustic beam was avoided [34]. The number of elements in the array determines the array size which is proportional to the lateral resolution of the system. An array with 50 elements was used corresponding to the total array length of 12.5 mm that results in 1.25 mm beam diameter at 29 mm away from the center of the array. The 29 mm length corresponds to the distance between the transducer array and the bolted joint. This 1.25 mm beam diameter provides sufficient resolution for imaging the bolted joint.

Several bolt tension values were compared. During the experiments, the torque applied to the bolt was precisely controlled as it is indirectly related to the bolt tension. Torque and tension are related by the bolt diameter and a friction factor which is a function of screw type and the materials used [1]. However, it is worth noting that for a particular bolt installed in a specific plate, the torque and tension are directly proportional. Also, as RAC is directly proportional to tension, torque and RAC values are also proportional to each other:

$$T \propto F_T \text{ and } RAC \propto F_T \text{ then } RAC \propto T \quad (8)$$

where T is the torque applied to the bolt and Fr is the bolt tension.

For the 6.3 mm (¼ in) grade 8 bolt used, the values of the friction factor and bolt yield strength are 0.18 and 691 N/mm², respectively, with the tensile stress area and nominal diameter being 20.5 mm² and 6.3 mm, respectively [33]. Thus, the maximum allowable torque for the bolt can be obtained as 13.78 Nm. Five (5) torque values equally spaced from 0 Nm to 13.78 Nm are selected for conducting the experiments. A torque wrench with 29 Nm of maximum capacity and 0.11 Nm of resolution was used to apply the required torque.

Experimental Procedure

1. The steel plate should be locked with help of C clamps. The rotation of the plate must be constrained during the tightening process.

2. The wedge-transducer assembly should be secured to the translator stage (TS), which helps create the synthetic phased array, with help of the Aluminum L and aluminum plate. The height of this assembly must permit the contact between the transducer base and the plate surface. Acoustic couplant must be applied prior to any contact as the acoustic impedance mismatch between the transducer crystal and the steel may prevent the transmission of waves.

Figure 5C:
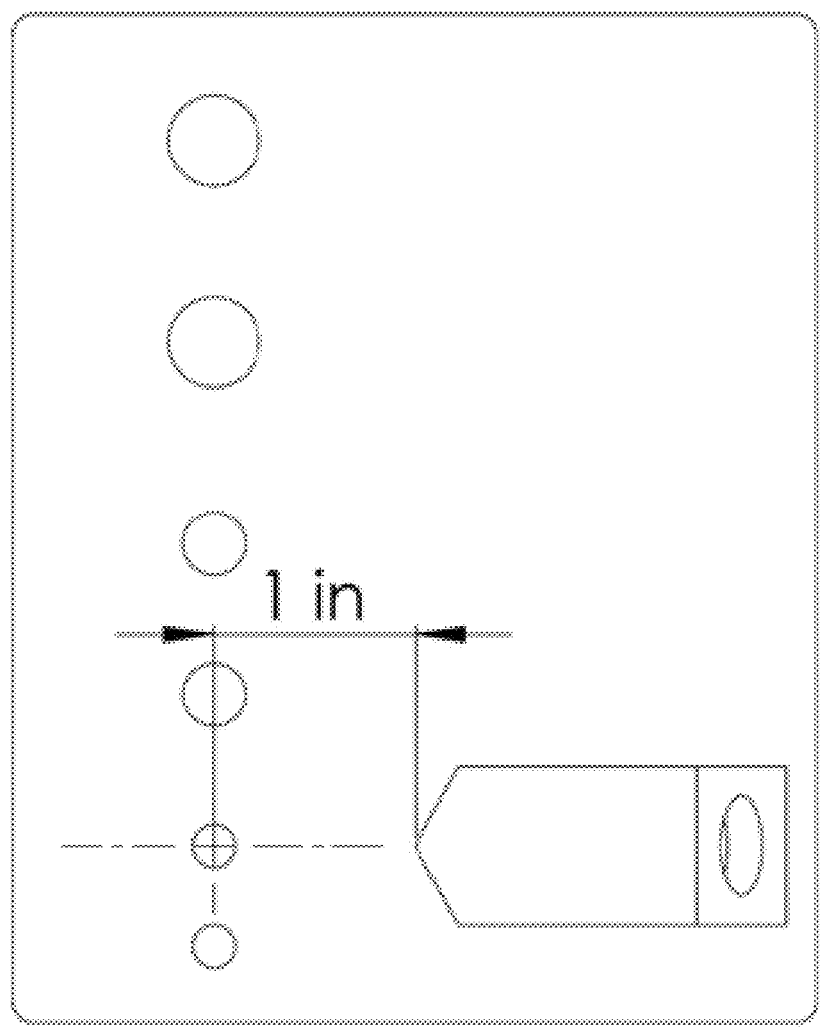
FIG. 5C is a schematic illustration of the wedge in an initial position in Example 1.

3. The TS is employed to position the wedge as is shown in FIG. 5C. The movement span of the TS is only one inch, so the positioning process should take into account that the wedge needs to move 0.5 in after initially positioned.

4. The oscilloscope and the pulse generator should be turned on. The signal gain was set around a value in the range of 30s or 40s. The correct configuration of the oscilloscope allows the edge reflection to be observed. The highest peak should be at least half of the oscilloscope scale.

5. In order to start the recording process, the signal was set to average. This helps to increase the signal to noise ratio of the system. After recording the signal at the initial point, the transducer was moved 0.01 in to the right; prior to recording the second response, the average function was reset. This procedure was repeated until 50 data are collected.

6. After the first 50 data were collected, the bolt was tightened with the torque wrench until 3.61 Nm was reached. This was the starting point for a new set of 50 data. The torque was increased in intervals of 3.61 Nm until the maximum decided value was achieved (17.17 Nm). Five (5) sets of 50 data were saved before the experiment was finished.

Results

The images of the bolt boundary were obtained for each of the five (5) different torque levels (with 3.61 Nm torque increments); the experimentally obtained reconstructed images with these different torque levels are given in FIGS. 6A-6E using the dynamic range 15 dB. In these figures, the horizontal (range) and the vertical extensions of each image are 2.37 cm×2.54 cm, respectively. The range extension of the image was 0.92 cm to 3.29 cm and the vertical extension was from −1.27 cm to +1.27 cm where the transducer array is located at the origin.

As can be observed in FIGS. 6A-6E, there was a clear change and trend in the shape of reconstructed images, especially the location of the first reflection from the bolted joint, when different torque values are applied. The array is located to the left of the image. It was observed that increasing the applied torque resulted in displacement of the first reflection boundary towards the transducer array; in other words, the boundary is closer to the array at higher torque values. Furthermore, even in the reference condition of no torque, a clear reflection from the plate hole was observed. It should also be pointed out that even with a very loose tightening of the bolt (corresponding to torque value 3.61 Nm in FIG. 6B), a noticeable movement of the reflective boundary towards the left side of the image is observed. As the applied torque is increased, images became noisier due to increase in the real area of contact, though there was a similar trend of movement of the reflective boundary towards the array. It can also be observed that the brightness of the images increases as the torque is increased since the response is getting stronger.

Figure 7A:
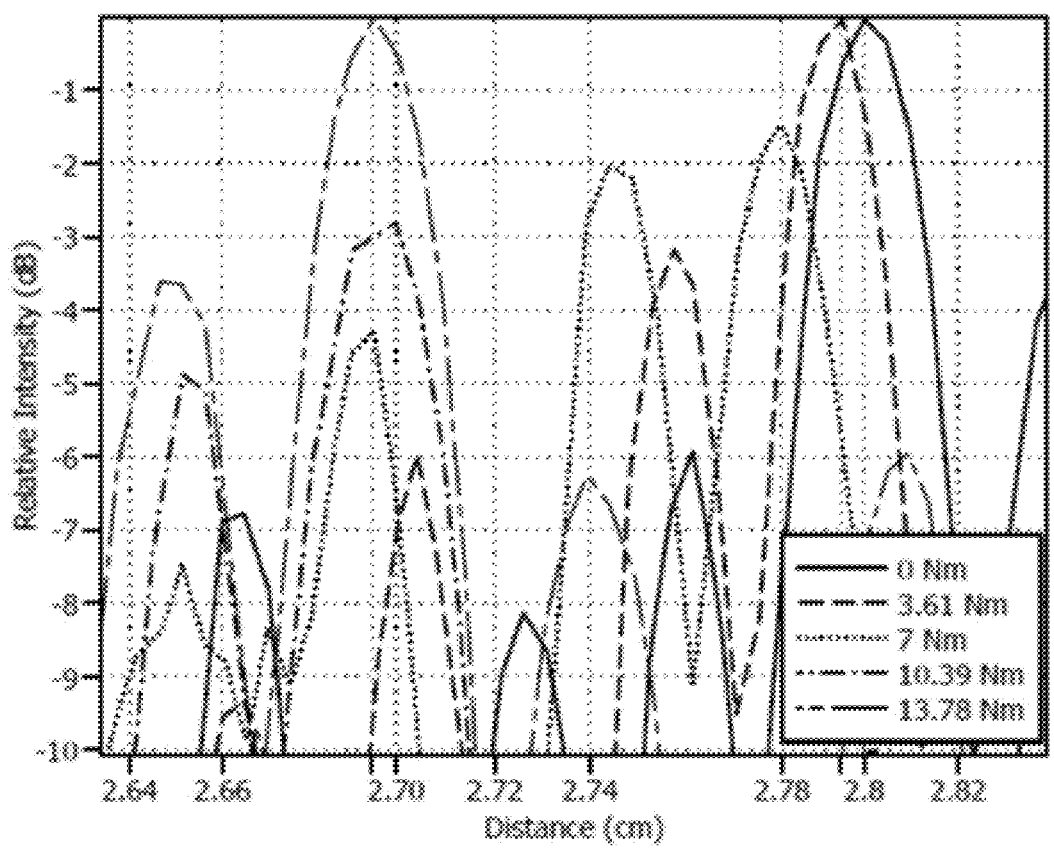
FIG. 7A is a graphical illustration of averaged 1-D images at 6 dB in Example 1.

The distances are measured for each torque value using FIG. 7A. The distance between the boundary and the array is measured 2.8 cm while there is no bolt. The distance difference corresponding to the highest torque value (13.78 Nm) and the lowest torque value (0 Nm) is about 0.12 cm, which is close to washer width. Other torque plots are between these two more extreme values.

To quantify the displacement of the first reflection boundary from the joint center towards the transducer array as a function of applied torque (i.e., the distance between the array and the bolt boundary), the relative average signal intensity of the reconstructed images as a function of distance from the transducer array (i.e., the lines around the bolt boundary) is plotted in FIG. 7A, where the horizontal axis is the depth and the vertical axis is the relative intensity. The 1-D average plot (FIG. 7A), which is a simplification of the 2-D reconstructed images (FIGS. 6A-6E), is obtained by taking the average of lateral dimension of the 2-D image. The 1-D plot allows establishing the exact position of the maximum intensity point of the 2-D image. The position of this point is used to estimate the actual distance change of the reflective boundary.

Figure 7B:
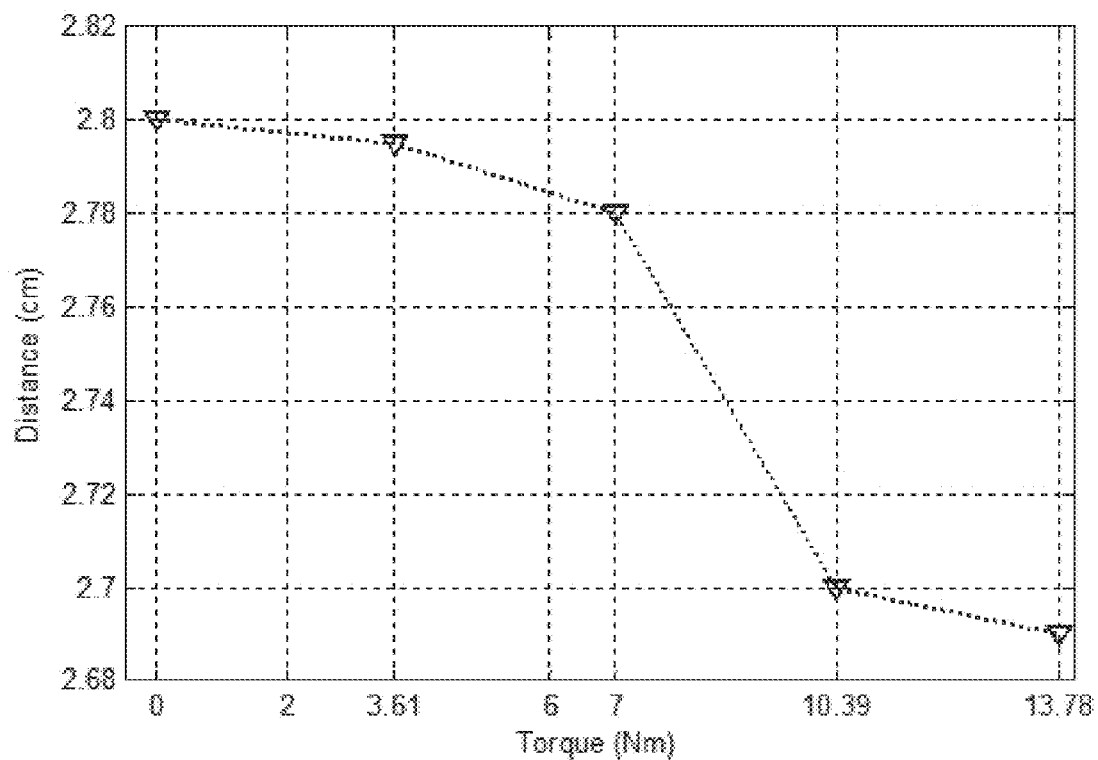
FIG. 7B is a graphical illustration of the torque applied versus the position of the acoustic wall in Example 1.

FIG. 7B illustrates the position of the first reflection boundary as a function of the applied torque (i.e., the distance of the boundary (peak position) versus torque values). This is the change in distance product of torque variation. Three (3) regions can be clearly seen: two (2) saturation regions around maximum and minimum torque and one (1) linear region between them. These measurements show the direct relation between the boundary distance and the torque value.

One can clearly observe from the maximum intensities of the reconstructed images that there is a clear trend of moving the reflection boundary towards the transducer array as the torque is increased. It can also be observed from FIG. 7B that the distance between the position of first reflection boundary with no torque applied (0 Nm) and maximum allowable torque (13.78 Nm) is about 0.11 cm. In other words, this is a reduction of 0.11 cm in the boundary separation as the torque is increased from 0 Nm to 13.78 Nm.

The first reflection boundary corresponding to rest of the torque values are positioned between these two extreme values. The first reflection boundary position change does not have a linear trend with increasing torque increments, as can be observed in FIG. 7B. This behavior can be explained by the fact that with this phased array image reconstruction technique, the location of the first reflection boundary, not the RAC, is being quantified/measured. The size of the characteristic length can be estimated with the image. As a result, the boundary distance and the torque should not be expected to have a linear relationship.

This non-linear variation of the movement of the first reflection of boundary as a function of applied torque can be used to estimate the torque (and thus the tightening of the bolt) by obtaining the distance of the first reflection boundary from the transducer array. An important characteristic of FIG. 7B is that RAC saturation appears to take place around 10.39 Nm corresponding to first reflection boundary position of about 2.7 cm. At this point, the washer edge is located at about 3.335 cm (the washer radius is 0.635 cm). This behavior can be explained by the bending suffered by the washer, which influences the growth of the RAC.

Error Estimation

In order to analyze the error associated with the generated images, it is necessary to measure the signal to noise (SNR) ratio of the received signals (A-scans). The foregoing results indicate that this method is not only capable of clearly distinguishing properly bolted joints from loosened joints but also capable of quantifying how loose the bolt actually is. It was determined that the SNR value for the entire bolt tension range was sufficient for image reconstruction.

Figure 8A:
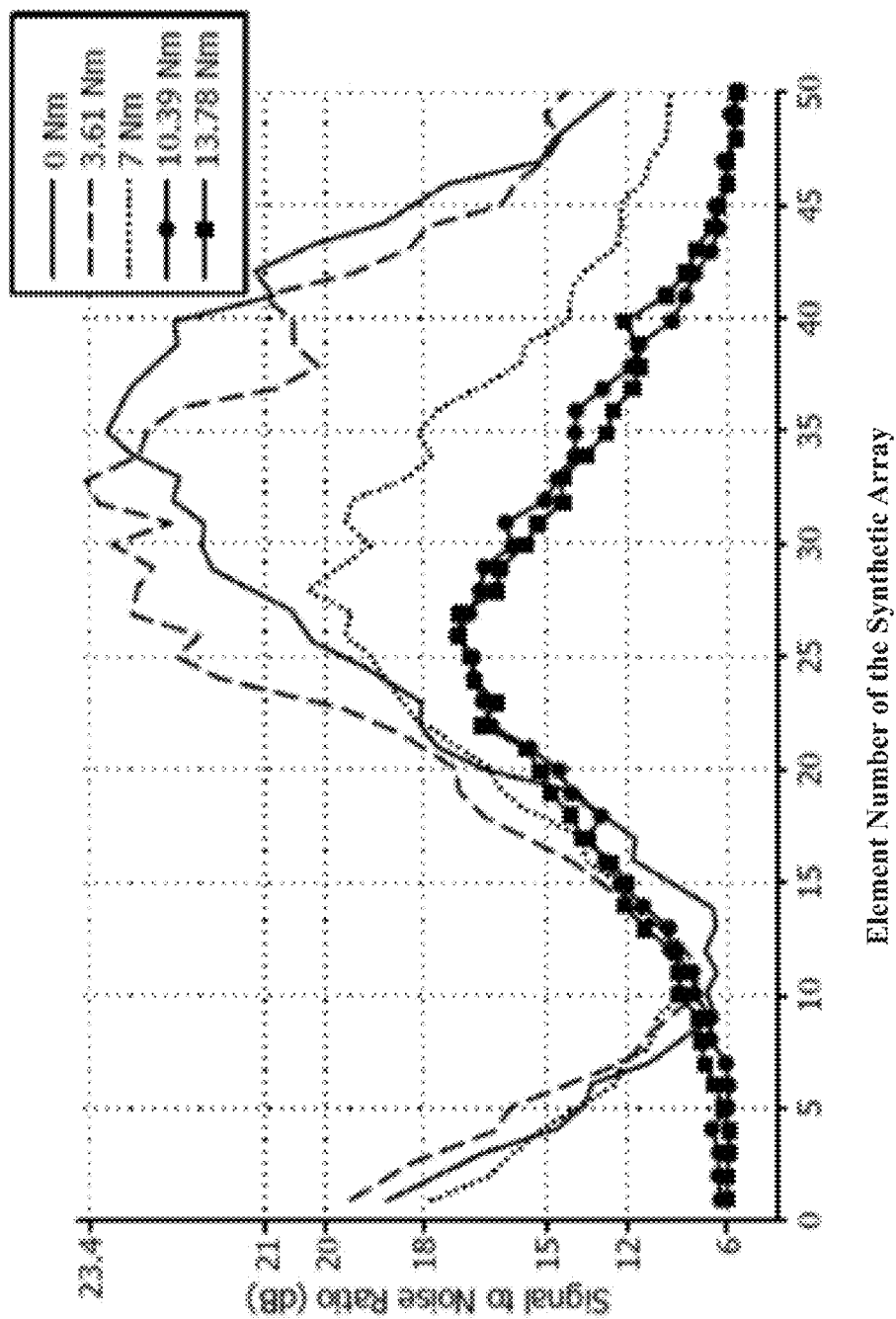
FIG. 8A is a graphical illustration of signal-to-noise ratio of the bolt reflections based in original signals.

Synthetic phased array modality was used, rather than phased array modality, for simplified beamformer design. However, one drawback of synthetic phased array modality is its lower SNR ratio. In order to ensure that SNR associated with the generated images was sufficient, the SNR of all received signals (A-scans) was studied. In FIG. 8A, the SNRs of the signals reflected by the bolt are presented. This figure illustrates the SNR levels for the 50 signals corresponding to each position of the transducer. Higher SNR values were obtained closer to the center position due to the reflections from the washer (or the hole). It was also observed that average SNR decreases with increasing torque levels. Thus, lower SNR values resulted in lower quality images for higher torque levels compared to lower torque values. Lower image quality may potentially lead to less accurate estimation and higher errors. However, the image quality was sufficient and may be increased by utilizing phased array modality.

Figure 8B:
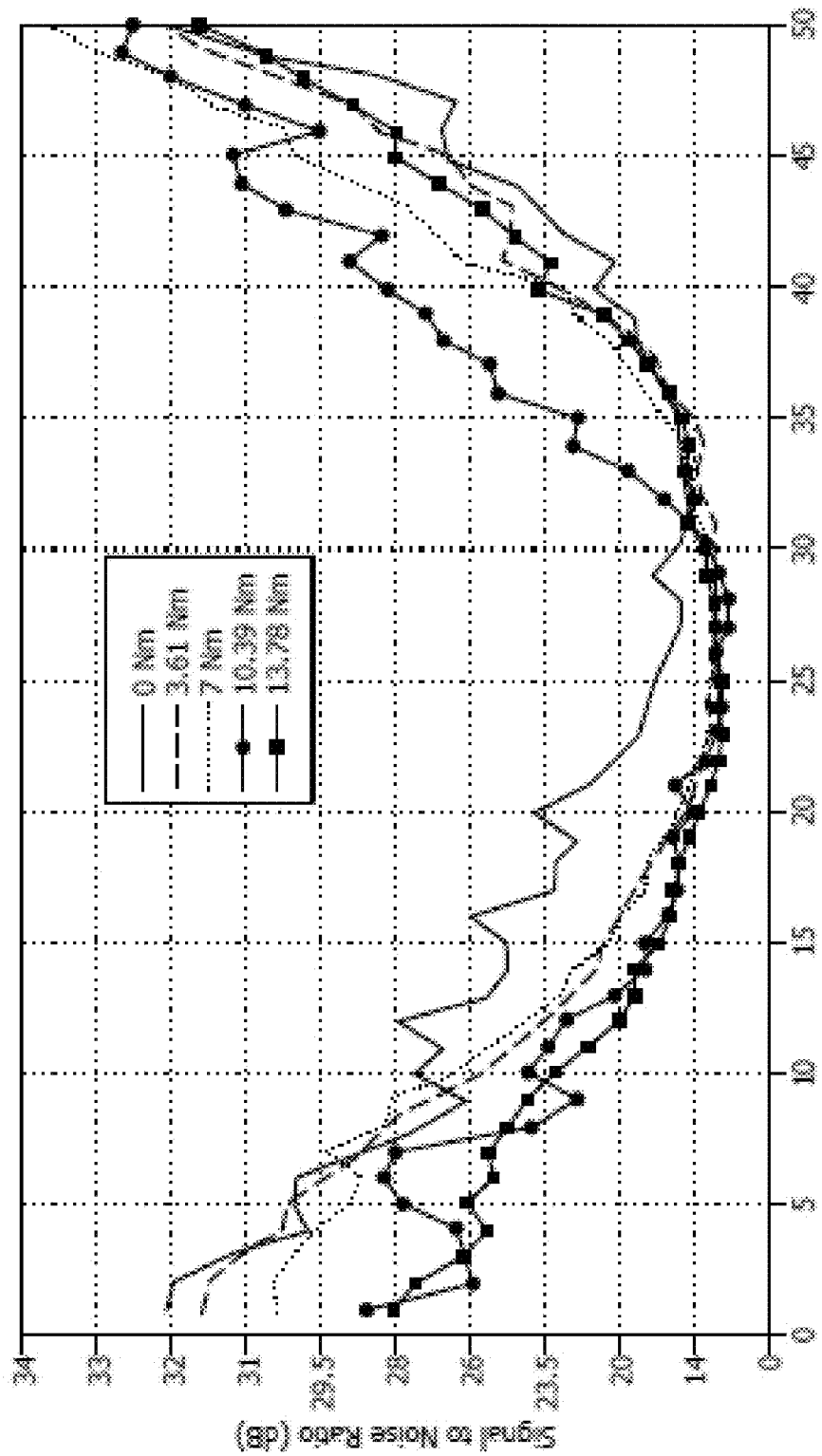
FIG. 8B is a graphical illustration of signal-to-noise ratio of the plate edge reflections based in original signals.

The minimum dynamic range that can be applied to the images was determined by the averaged SNR. The reflective boundary position was calculated using the 1-D averaged plot based on the location of the signal peaks. Consequently, the peak SNR value of FIG. 8B at each torque level corresponds to the peaks in FIG. 7A. The minimum peak SNR of the system was around 17 dB at 13.78 Nm, as shown in FIG. 8A. Although this is not a desired SNR level, it is sufficient for differentiating the signal from the ambient noise.

The averaged signal to noise ratio for each torque value is depicted in Table 2 for reference:

TABLE 2

Experimentally obtained SNR ratio for different torque values applied to the bolted joint.

| Torque Level (Nm) | 0 | 3.61 | 7 | 10.39 | 13.78 |
|---|---|---|---|---|---|
| Average SNR (dB) | 18 | 18.31 | 15.75 | 12 | 12.05 |

The decrease of SNR can clearly be seen as the applied torque is increased. The average SNR value of the system is around 15 dB. This SNR level was sufficient for differentiating the signal from the ambient noise. The reduction of the SNR of the system around the bolt may be attributed to some attenuation due to the bolt interference. The maximum SNR are presented in the signals of the array sides, while the minimum SNR are in the center.

Figure 8C:
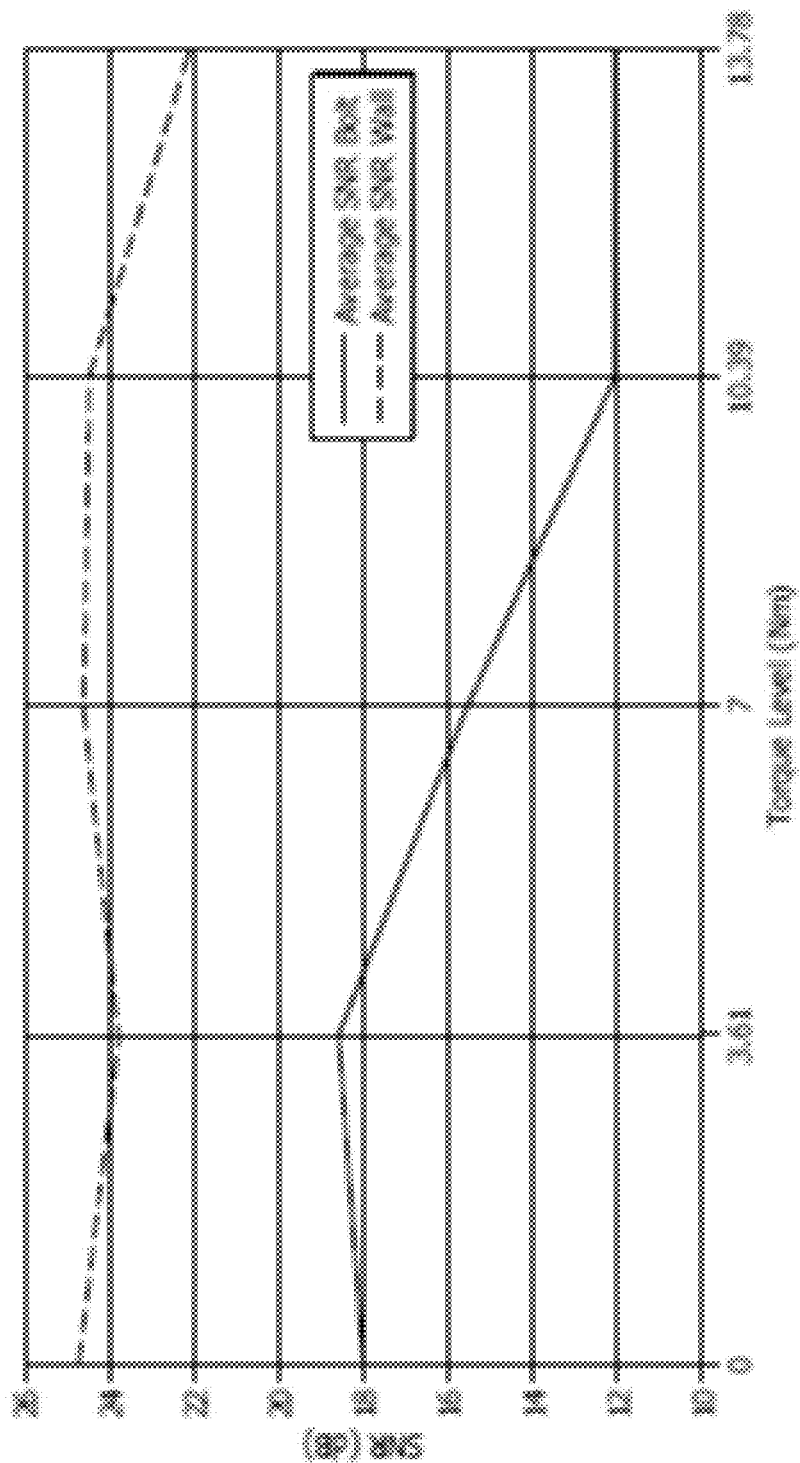
FIG. 8C is a graphical illustration of averaged signal-to-noise ratio of the bolt and plate edge reflections based in original signals.

In the case of the plate edge, the behavior of the SNR peaks is not as clear as in the case of the bolt reflections. With the intention of comparing them, a graph of the averaged SNR for both cases is presented in FIG. 8C. Even though the signal loss tends to reduce the SNR for both cases as the torque is increased, there is an abrupt SNR drop in the bolt case. It is especially notorious when the torque is increased from 3.61 Nm to 10.39 Nm and the SNR decreases from 18 dB to 12 dB.

This analysis permits identification of the existence of error sources that generate signal losses, which would lead to a reduction in the SNR of the system. For instance, the acoustic couplant can be inducing signal loss as the experiment is performed. The necessity to move the transducer with the couplant may be causing traces of gel to interfere with the wave propagation. Additionally, the movement in the set up caused by the tightening process may cause signal reduction.

The axial resolution of the system permits the establishing of accuracy of the system to estimate the movement of the reflective boundary. The frequency response and temporal pulse length of the system were founded with a network analyzer, and the resulting axial resolution of the system was found to be 0.072 cm. The axial resolution is close to half of the total change in the boundary position (0.12 cm), meaning that the imaging system employed has the capability to measure the boundary position changes with sufficient accuracy.

The imaging system utilized in Example 1 has the correct SNR and enough axial resolution for the investigation of RAC changes due to bolt tension in a ⅜ inch bolt. A minimum SNR peak of 17 dB is founded at the maximum torque level, while a boundary movement of 0.12 cm is measured with an axial resolution of 0.07 cm. Increasing the precision of the system may be accomplished by higher frequency and higher damped transducers. Additionally, a phased array can increase the SNR and may limit the interferences of acoustic couplant caused by the mechanical movement of the transducer.

CONCLUSION

In this Example, the current invention fabricates a bolt tension sensor based on surface acoustic waves. The bolt tension was estimated using the reflection of SAWs created by the bolted joint interference. This methodology measured the health of the bolted joints. Images were constructed using the SAW echoes from boundary to enable distant measurement. Thus, this methodology makes the quantification feasible since the simultaneous imaging of more than one bolt distantly is enabled. These results permit the precise measurement of the health of the bolted joints. The design of a phased array can enhance image quality.

The results indicate that this method is not only capable of clearly distinguishing properly bolted joints from loosened joints but also capable of quantifying how loose the bolt is. Increase in the bolt tension resulted in an increase in the number of points of that are in-contact at the bolt-plate interface (real area of contact). This increase in the real area of contact caused the first reflection boundary position change measured from the bolted joint by using surface acoustic waves. The boundary location change was quantified by using a 1-D and 2-D ultrasonic images obtained by linear synthetic array image processing technique.

The 2-D ultrasound imaging allowed clear and detailed visualization of the position of the reflective boundary when applied torque to the bolt was changed. For the entire range of torque values from zero to maximum allowable, increase in the torque value increased the real area of contact and therefore moved the position of the reflective boundary towards the ultrasonic array. The boundary position versus the torque applied to the bolt was also investigated. There were two distinct regions; the first region presented a non-linear behavior, while the second one was identified as a saturation region. The saturation region (presented at the highest torque values) was characterized by negligible change in the boundary position due to further increase in the torque applied.

The signal-to-noise (SNR) analysis was also performed and the results indicate that the intensity of the signal was reduced as the torque was increased. However, it should be noted that the SNR value even for the maximum allowable torque value was sufficient for image reconstruction. The bolt tension sensor investigated here has the potential to be used as a component in a non-destructive structural health monitoring (SHM) system for local monitoring of civil infrastructures.

In situations where the underlying structure does not allow direct access to the bolts by the wedge, sensor arrays can be directly integrated into the structure. Wireless interrogation can then be employed for data acquisition. Surface condition is also an important factor that may affect the operation. Surface conditions at the plate-bolt and plate-wedge interface (such as contamination, surface roughness) and along the propagation path (e.g., liquid loading) may possibly cause minor problems such as wave attenuation, undesired scattering. However, it should be noted that these issues can be overcome by using proper commercially available surface treatments and ultrasonic couplants.

Example 2

Tension Evaluation of a ¼ inch Stainless Steel Bolt

This example tests a stainless steel bolt of ¼ in diameter installed in a 1018 steel plate. As the RAC growth affects the position of the SAW main reflections, it is necessary to establish very precisely where those reflections take place. It was determined that a synthetic phased array imaging method was effective for detecting the location of very small holes in a steel plate, producing reconstructed images with accurate longitudinal resolution. Thus, this imaging system was used in this particular example.

Experimental Design

A synthetic phased array (SPA) is employed in the following experiments. A transducer with central frequency of 5 MHz, diameter of 0.5 in and an array pitch (p) of approximately ¼ of the wave length ($\lambda/4$) was selected to aim for high longitudinal resolution. The longitudinal position of the acoustic wall was used to characterize the RAC changes, necessitating high longitudinal resolution. The elementary pitch was calculated as follows:

$$p = \lambda/4 = \frac{v_{SAW}}{4f} = \frac{\sqrt{\frac{G}{\rho}\left(\frac{0.87 + 1.12v}{1+v}\right)}}{4f} \quad (9)$$

$$p = \frac{\sqrt{\frac{80Gpa}{7870 \text{ kg}/m^2}\left(\frac{0.87 + 1.12 \times 0.29}{1+0.29}\right)}}{4 \times 5 \text{ MHz}}$$

$$p \approx 0.01 \text{in}$$

where f is the transducer center frequency, G, v, $\rho$ are respectively the shear modulus, the Poisson's ratio and the density of the 1018 steel. Properties were taken from [50].

The number of elements in the array (NE) determines the array aperture (length), which is proportional to the lateral resolution. Thus, a high number of elements increases the resolution, at a cost of increasing scanning time, so a balance between image quality and experiment duration should be determined. An array of 50 elements was created, so the array has an active aperture of 0.5 in.

Figure 9A:
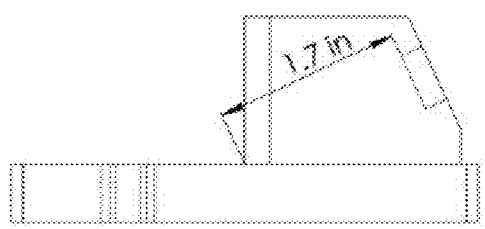
FIG. 9A is a side view of transducer-wedge position with respect to the targeted hole, as implemented for an embodiment of the current invention in Example 2.
Figure 9B:
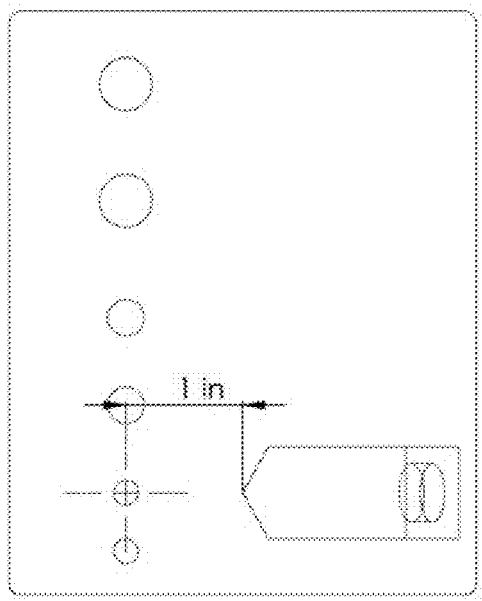
FIG. 9B is a top view of the system of FIG. 9A.

In addition to the array aperture, the distance to the target also affects the image lateral resolution. The best resolution is achieved with a separation equal to the transducer natural focus (NF). The NF is the point of maximum transverse relative intensity within the focal area. Due to the presence of the wedge, the distance to the target (AP) is founded by subtracting the space inside the wedge (1.7 in):

$$AP = N - 1.7 \text{ in} = \frac{D^2 f}{4f} - 1.7 \text{in} \quad (10)$$

$$AP = \frac{0.5 \text{in}^2 \times 5 \text{ MHz}}{4 \times 2953 \, m/s} - 1.7 \text{in}$$

$$AP = 1.0 \text{in}$$

where D is the transducer diameter, f the transducer's center frequency, c is the SAW speed in 1018 steel, NF is the transducer's natural focus and AP the array position with respect to the bolt. FIGS. 9A-9B illustrate the final configuration.

Stretching the bolt increases the bolt tension and hence increasing the RAC between the bolt head and the steel plate. It discussed previously the RAC and the normal force are proportional [12]. The bolt tension is equivalent to the normal force in this application: the elongation of the bolt body creates a pulling force at the bolt head, but is also the deformation in the bolt body which creates the tension force. In this sense, the tension force pulls the bolt head against the plate in the same as the normal force would push it.

In this experiment, the bolt tension was not directly controlled, but the torque applied to the bolt was controlled. Torque and tension are related by the bolt diameter and a friction factor, which is a function of screw type and the materials in contact.

From this perspective, for a particular bolt installed in a specific plate, the torque and tension are proportional in nature. As a result, the torque and RAC values are also proportional:

$$T \propto F_N \; \tilde{} \; RAC \propto F_N$$

Then $$RAC \propto T \quad (11)$$

where T is the torque applied to the bolt, $F_N$ is the normal force and RAC is the real area of contact.

One can infer from this equation that the RAC can be adjusted by controlling the specific amount of torque applied to the bolt. In this Example, three torque levels were applied: no torque, medium torque, and maximum torque.

Experiment Configuration

There are three key components in the experiment setup: precise position controlling system, SAW generation system and the bolted joint. The position control of the transducer-wedge attachment is achieved through a manual translator stage with resolution of 0.001 in and maximum displacement span of (one) 1 in. The transducer and the wedge are adapted to the translator stage (Thorlabs PT3) by specially designed aluminum parts.

The electronic signals are generated and received by a pulse generator (Olympus 5072PR) and an oscilloscope (Tektronix TDS 2024B). A 5 MHz piezoelectric transducer (PZT) with circular aperture of ½ in is driven by the pulse generator. A crystal wedge is attached to the PZT for creating SAW in the steel plate. The configuration of the devices is presented in Table 3.

TABLE 3

Parameters employed in the experimental configuration.

| | |
|---|---|
| Pulse generator damping | 50 Ω |
| Pulse generator PRF | 200 Hz |
| Amplification | 45 dB |
| Pulse generator LPF (1 MHz) | ON |
| Pulse generator HPF (10 MHz) | ON |
| SAW velocity | 2590 m/s |
| Transducer frequency | 5 MHz |
| Transducer diameter | 0.5 in |
| Array pitch (in) | 0.01 in |
| Number of elements | 50 |
| Target distance | 2.7 in |
| Bolt diameter | 0.5 in |

Figure 10A:
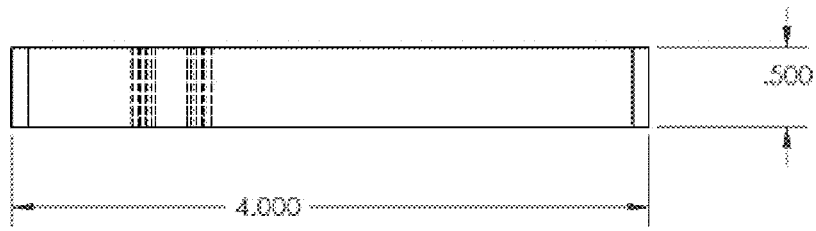
FIG. 10A is a side view of a 1018 steel plate.
Figure 10B:
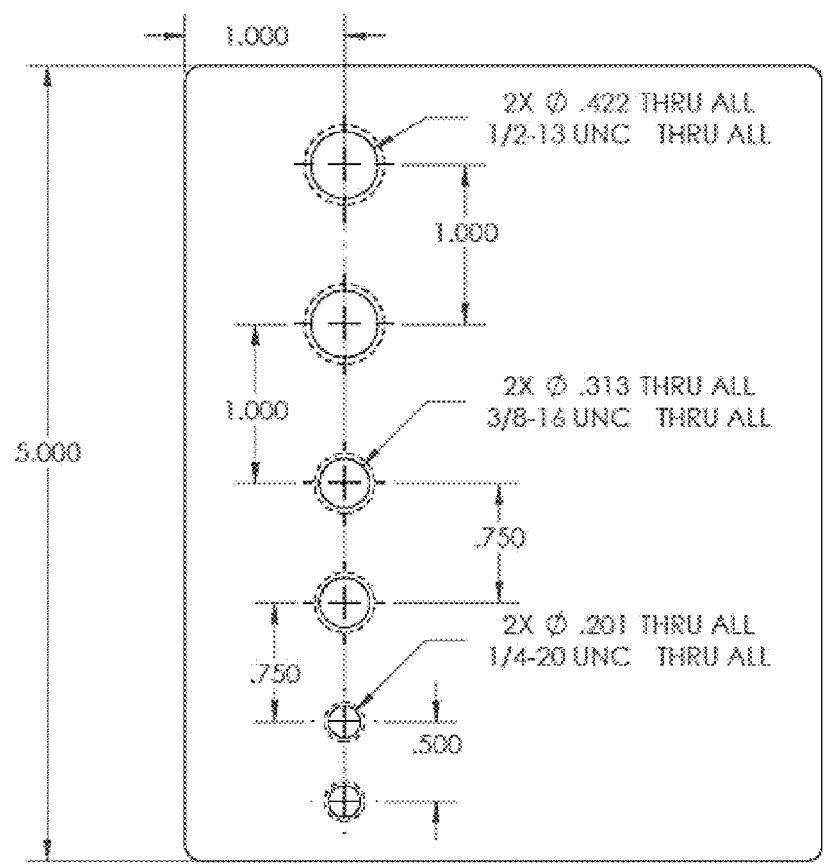
FIG. 10B is a top view of the steel plate of FIG. 10A.

The bolted joint employ in this test is formed by a 1018 steel plate and a ¼ in 20UNC bolt. Neither nut nor washer is used in this test. The bolt is tightened with help of the threaded holes present in the work bench. In FIGS. 10A-10B, dimension and characteristics of the machined holes are illustrated. All the holes in the plate have a coarse thread. This characteristic facilitates the installation of the tested bolts. Additionally, no lubricant is used in the joint. The surface conditions of the threads are good enough to permit proper bolt tightening. The plate can be attached to the work bench by C-clamps when is so required.

Experimental Procedure

A synthetic phased array is created by the mechanical movement of a single transducer. All signals were averaged to increase the signal to noise ratio of the system.

The experimental procedure was as follows:

1. The steel plate should be locked with the help of C clamps. The rotation of the plate must be constrained during the tightening process.

2. The wedge-transducer assembly should be secured to the TS with help of the aluminum L and aluminum plate. The height of this assembly must permit the contact between the transducer base and the plate surface. Acoustic couplant must be applied prior any contact as the acoustic impedance mismatch between the transducer crystal and the steel may prevent the transmission of waves.

3. The TS is employed to position the wedge as is shown in FIGS. 9A-9B. The movement span of the TS is only one (1) inch, so the positioning process took into account that the wedge needs to move 0.5 in after initially positioned.

4. The oscilloscope and the pulse generator were turned on. The signal gain was set around a value in the range of 30s or 40s. The correct configuration of the oscilloscope allows the edge reflection to be observed. The highest peak should be at least half of the oscilloscope scale.

5. In order to start the recording process, the signal recording mode should be set to average; this helps to increase the signal to noise ratio of the system. After recording the signal at the initial point, the transducer should be moved 0.01 in to the right; prior to recording the second response, the average function should be reset. This procedure is repeated until 50 data are collected.

6. After the first 50 data are collected, the bolt should be installed and tightened with a wrench until a medium torque value is achieved. This is the starting point for a new set of 50 data. Before the third data set is recorded, the bolt should be tightened until a maximum torque value is achieved. This, in turn, is the starting point for a new set of 50 data.

Experimental Results

Figure 11A:
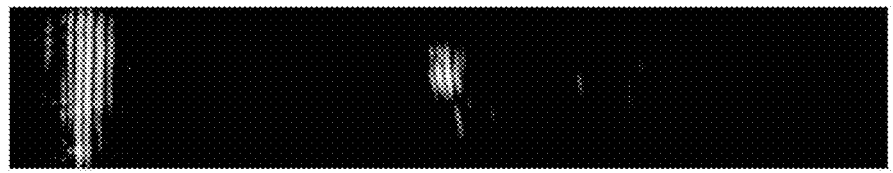
FIG. 11A is an image of a steel plate generated at 15 dB of dynamic range with no applied torque.
Figure 11B:
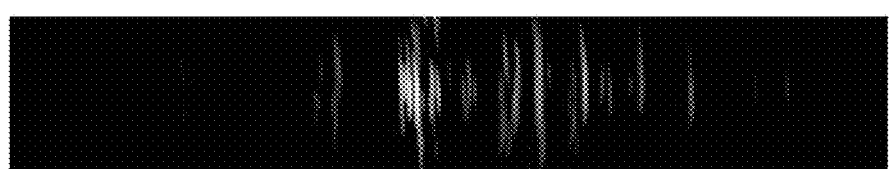
FIG. 11B is an image of a steel plate generated at 15 dB of dynamic range at a medium level of applied torque.
Figure 11C:
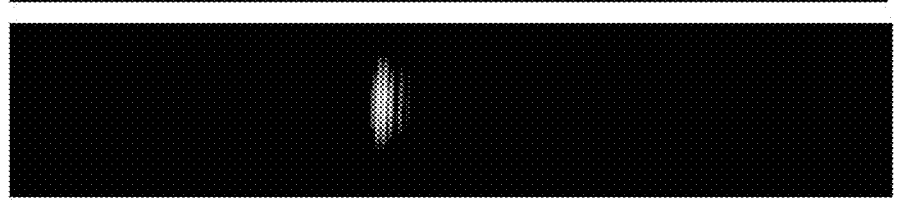
FIG. 11C is an image of a steel plate generated at 15 dB of dynamic range at a maximum level of applied torque.

The imaging reconstruction generates three images correspondent to the applied torque levels. FIGS. 11A-11C illustrate the results as 15 dB of dynamic range at no torque, medium torque, and maximum torque, respectively. The array is located to the left of the image. In the center of the images, the reflections from the bolt head are clearly distinguishable.

The position of the bolt reflection has clearly an influence from the applied torque. As expected, at higher torque levels the reflections move gradually closer to the array (to the left). Furthermore, the images appear to be sharper in the extreme cases of maximum and minimum torque.

Figure 12:
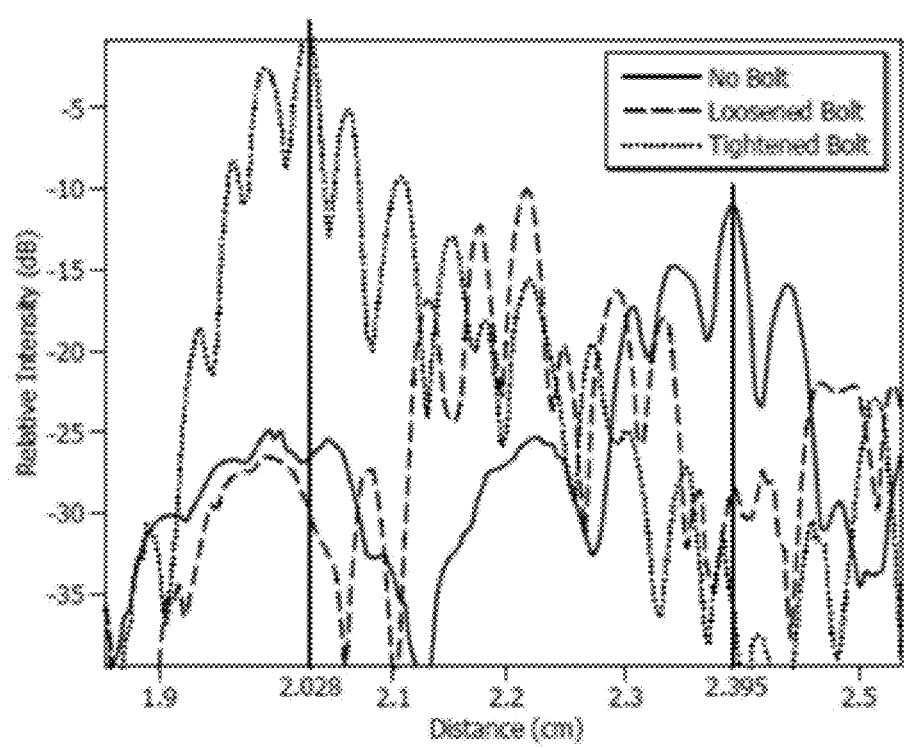
FIG. 12 is a graphical illustration of averaged 1-D images at 6 dB in Example 2.

An averaged 1-D images are illustrated in FIG. 12. The plot is a portion of the complete 6 dB image averaged transversally. This figure allows easier calculation of the position of the main objects in the 2-D images. In FIG. 12, the positions of the bolt head reflections are presented and compared. The position difference with respect to the no-bolt versus tightened-bolt cases is:

Tightened Bolt=2.395−2.028=0.367 cm

Loosened Bolt=2.395−2.2=0.195 cm

Example 3

Tension Evaluation of a ½ Inch Stainless Steel Bolt

This example tests an exemplary embodiment of the current methodology with a ½ inch 13UNC stainless steel bolt. The larger bolt allows the application of higher tension levels. The larger bolt also increases the geometric area of contact, thus likely providing larger changes in the RAC.

Experiment Design

The parameters utilized in this example were array pitch, number of elements in the array, distance to the target, and the torque applied. The array pitch (0.01 in) is maintained because the same transducer was used (i.e., transducer with 5 MHz of central frequency and ½ in of circular aperture). Additionally, the target distance was also kept constant.

The array aperture is increased due to the target size. It is necessary to have a fixed boundary that works as framework to clearly establish the movement of the reflective boundary. The plate edge is used for this purpose. Then the array aperture is selected to be larger than the target. An aperture of 0.75 in was designated and so 75 array elements were needed.

The methodology proposed by [1] is used to calculate the maximum applicable torque for the ½ in 13UNC stainless steel bolt. A friction value of 0.2 is assumed as suggested by [1].

$$T = KA_t 0.855_y d = 0.20 \times 9.154824 \times 10^{-5} m^2 \times 35 \text{ ksi} \times \tfrac{1}{2} \text{ in}$$

$$T_{max} = 35.6 \text{ Nm} \quad (12)$$

where K is the friction factor, A, is the tensile stress area, S, is the bolt yield strength, d is the bolt nominal diameter and T is the torque applied.

The analysis was performed using the changes of the parameters of interest: tension, torque and boundary position. The uncertainties in the tension applied to the bolt, which depends on the friction and may vary up to 50% [62], do not affect the result analysis. RAC, tension and torque are proportional in nature, so the proportionality coefficients, such as friction in the case of torque-tension, influence the value of the parameters but do not influence the changes produced by them.

The maximum torque is higher than the torque supported by the torque wrench, so the maximum torque supported by the wrench is chosen. Additionally, due to the high number of array elements, the number of torque states were decided to be three with the maximum torque and torque increments decided as follows:

$$T_{max} = 29.03 \text{Nm} \quad (13)$$

$$T_{increments} = \frac{T_{max}}{3} \approx 15.48 \text{Nm}$$

Experiment Configuration

The position controlling system, SAW generation system are the same as the ones discussed in the prior section. The translator stage (Thorlabs PT3), the pulse generator (Olympus 5072PR) and the oscilloscope (Tektronix TDS 2024B) are also employed in this experiment. The 1018 steel plate is also kept but the ½ in threaded hole is used this time. The tested bolt is a ½ in 13UNC stainless steel bolt. Due to the bolt's size, a ½ inch stainless steel nut was employed to tighten the bolt. It was not necessary to apply lubrication. The configuration of devices is presented in Table 4.

TABLE 4

Parameters employed in the experimental configuration.

| | |
|---|---|
| Pulse generator damping | 50 Ω |
| Pulse generator PRF | 200 Hz |

TABLE 4-continued

Parameters employed in the experimental configuration.

| | |
|---|---|
| Amplification | 45 dB |
| Pulser LPF & HPF | ON |
| SAW velocity | 2590 m/s |
| Transducer frequency | 5 MHz |
| Transducer diameter | 0.5 in |
| Array pitch (in) | 0.01 in |
| Number of elements | 75 |
| Target distance | 2.7 in |
| Bolt diameter | 0.5 in |
| Bolt yield strength | 35 ksi |
| Friction factor | 0.20 |
| Tensile stress area | $9.154824 \times 10^{-5}$ m$^2$ |
| Maximum torque | 29.03 Nm |
| Torque increments | 15.48 Nm |

Experimental Procedure

1. The steel plate should be locked with help of C clamps. The rotation of the plate should be constrained during the tightening process.

2. The wedge-transducer assembly should be secured to the TS with help of the Aluminum L and aluminum plate. The height of this assembly must permit the contact between the transducer base and the plate surface. Acoustic couplant must be applied prior any contact as the acoustic impedance mismatch between the transducer crystal and the steel may prevent the transmission of waves.

Figure 13:
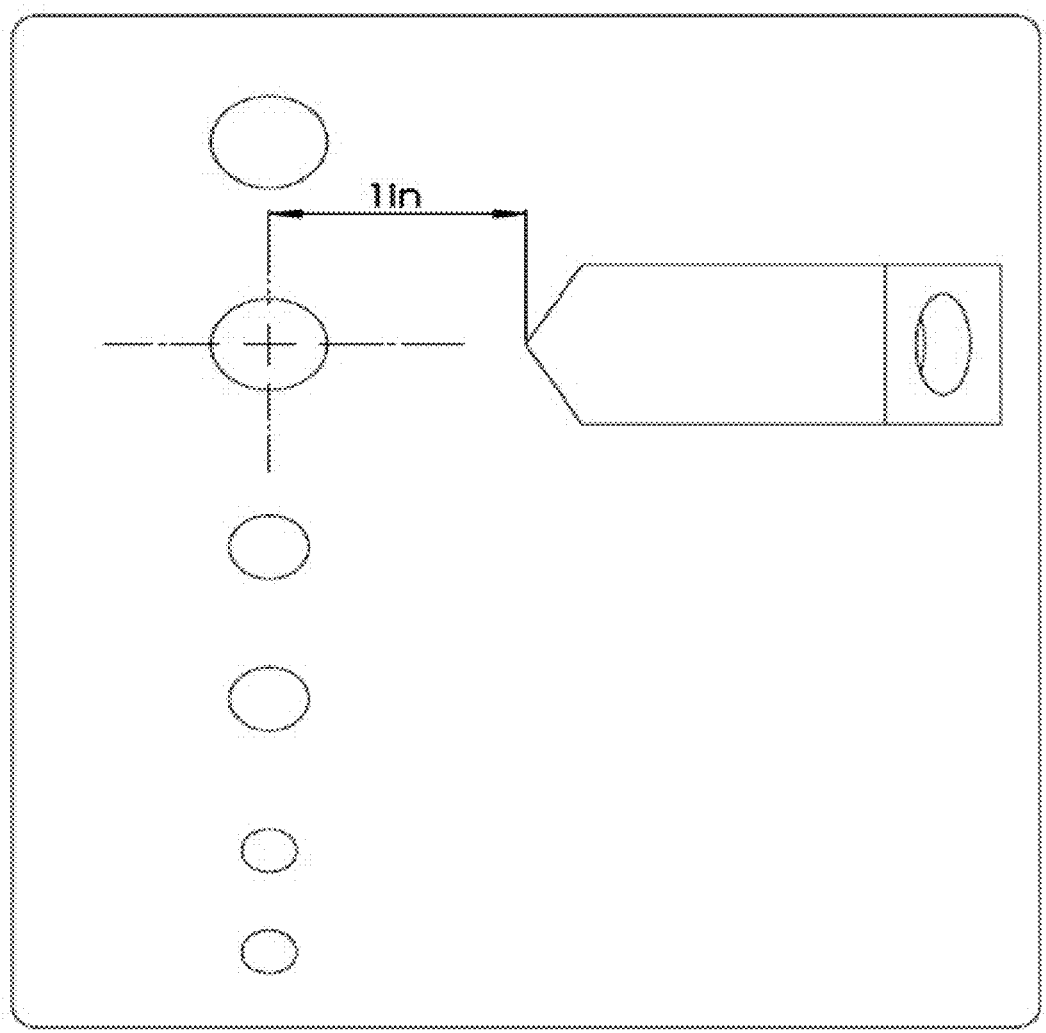
FIG. 13 is a schematic illustration of the wedge in an initial position in Example 3.

3. The TS is employed to position the wedge, as is shown in FIG. 13. The movement span of the TS was one (1) inch, so the positioning process took into account that the wedge needs to move 0.75 in after initially positioned.

4. The oscilloscope and the pulse generator should be turned on. The signal gain was set around a value in the range of 30s or 40s. The correct configuration of the oscilloscope allows the edge reflection to be observed. The highest peak should be at least half of the oscilloscope scale.

5. In order to start the recording process, the signal should be set to average, which helps to increase the signal to noise ratio of the system. After recording the signal at the initial point, the transducer was moved 0.01 in to the right. Prior to recording the second response, the average function was reset. This procedure was repeated until 75 data are collected.

6. After the first 75 data were collected, the bolt was tightened with the torque wrench until a 15.48 Nm torque value was reached. This was the starting point for a new set of 75 data. After the second 75 data were collected, the bolt was tightened with a torque wrench until a 29.03 Nm maximum torque value (maximum value supported by the wrench) was reached. This was the starting point for a new set of 75 data.

Experimental Results

Figures 14A, 14B, 14C:
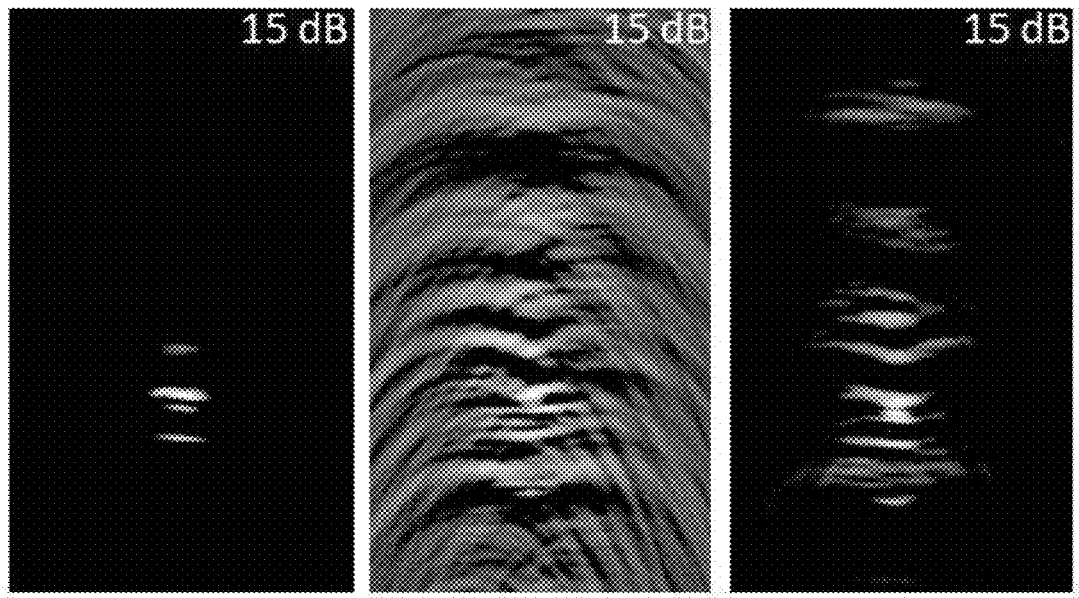
FIG. 14A is an image of a steel plate generated at 15 dB of dynamic range at 0 Nm of applied torque.
FIG. 14B is an image of a steel plate generated at 15 dB of dynamic range at 15.48 Nm of applied torque.
FIG. 14C is an image of a steel plate generated at 15 dB of dynamic range at 29.03 Nm of applied torque.

One image at every torque value was constructed. In FIGS. 14A-14C, the results are presented at 15 dB of dynamic range at 0 Nm, 15.48 Nm, and 29.03 Nm, respectively. In the images, the clear reflection from the hole and the nut can be observed, but the position variation in not clear.

Figure 15:
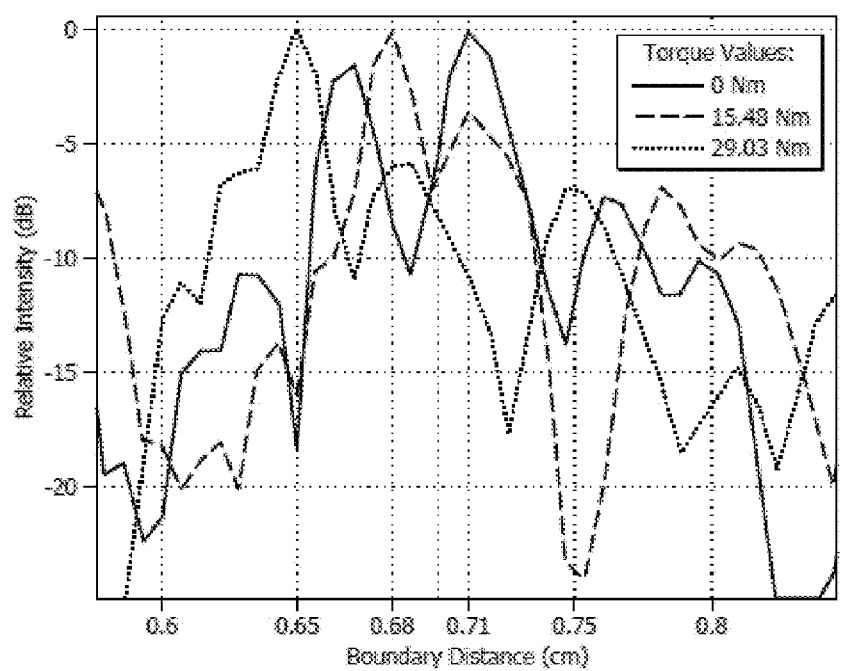
FIG. 15 is a graphical illustration of averaged 1-D images at 6 dB in Example 3.

FIG. 15 illustrates the average signal intensity of the reflected waves. With this figure, the change in the acoustic wall can be observed. The position change was 0.06 cm, which is very small compared to the diameter of the nut (1.88 cm).

Figure 16:
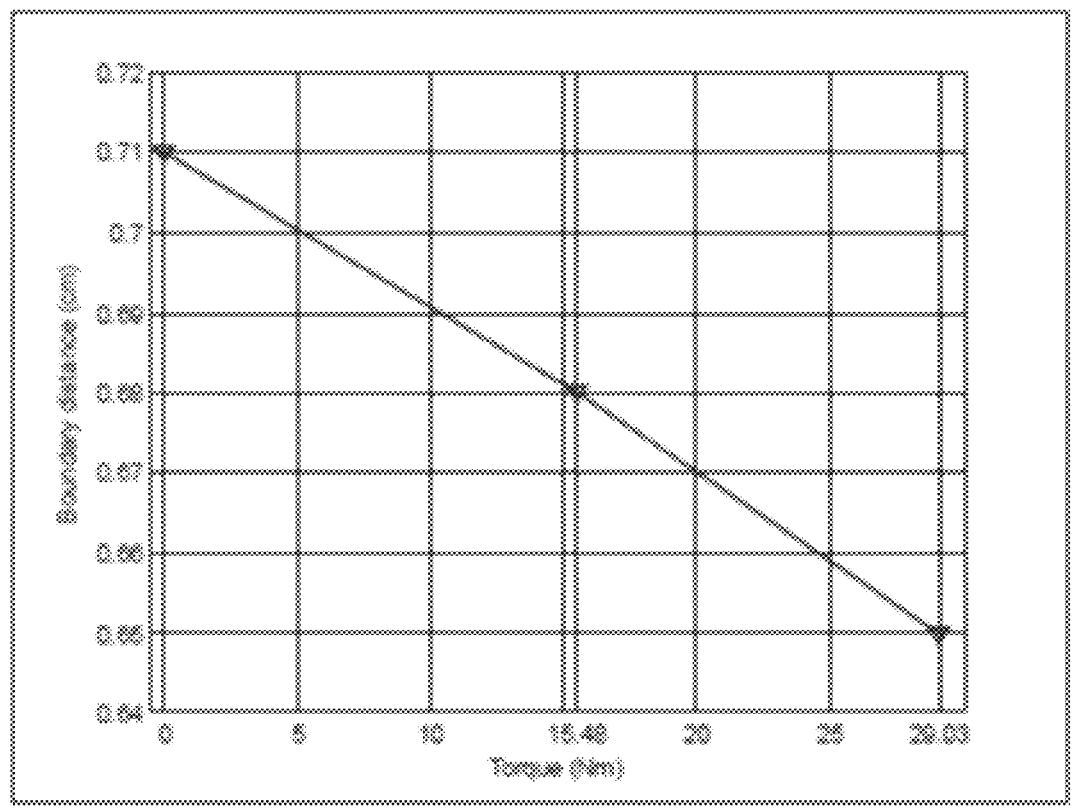
FIG. 16 is a graphical illustration of applied torque versus position of the acoustic wall in Example 3.

In FIG. 16, a plot of the boundary position against the torque is presented. The parameters were inversely proportional. The small change in the boundary position may be caused by lower force per unit area (pressure).

REFERENCES

[1] Budynas, R. G.; Nisbett, K. Screw, fasteners, and the design of nonpermanent joints. In Shigley's mechanical engineering design; 8th ed.; McGraw-Hill companies, Inc: Burlington, Mass., 2006; pp. 396-425.

[2] Hess D P, 1998, Handbook of Bolts and Bolted Joints (J. H. Bickford and S. Nasser, editors) (New York)

[3] Bickford. J. H. Introduction to the design and behavior of bolted joints; 4th ed.; CRC Press: Boca Raton, 2008.

[4] Goodier, J. N. Loosening by vibration of threaded fastenings. Mechanical Engineering 1945, 798-802.

[5] Sauer, J. A.; Lemmon, D. C.; Lynn, E. K. Bolts: how to prevent their loosening's. Machine Design 1950, 22, 133-139.

[6] Pai, N. G.; Hess, D. P. Experimental study of loosening of threaded fasteners due to dynamic shear loads. Journal of Sound and Vibration 2002, 253(3), 585-602.

[7] Pai, N. G.; Hess, D. P. Influence of fastener placement on vibration-induced loosening. Journal of Sound and Vibration 2003, 268, 617-626.

[8] Huang. Y. H.; Liu, L.; Yeung, T. W.; Hung, Y. Y. Real-time monitoring of clamping force of a bolted joint by use of automatic digital image correlation. Optics & Laser Technology 2009, 41, 408-414.

[9] Martinez Garcia, Jairo Andres. "A Novel Ultrasonic Method to Quantify Bolt Tension", University of South Florida, Graduate School Theses and Dissertations (2012).

[10] Johnson, K. L. Contact mechanics; Cambridge University Press: Cambridge Cambridgeshire; New York, 1985; p. 452.

[11] Fischer-Cripps A C 2000 Introduction to Contact Mechanics (New York)

[12] Czichos, H. Tribology: a systems approach to the science and technology of friction, lubrication and wear; Elsevier Scientific Publishing Company: New York, N.Y., 1978; Vol. I, pp. 45-176.

[13] Thomenius. K. E. In Evolution of ultrasound beamformers, Ultrasonics Symposium, 1996. Proceedings., 1996 IEEE, 3-6 Nov. 1996, 1996; 1996; pp. 1615-1622 vol. 1612.

[14] Hess, D. P. Vibration and shock-induced loosening. In Handbook of Bolts and Bolted Joint; Bickford, J., Ed. ASM International: New York, 1988.

[15] Pedinoff, M. E.; Waldner, M.; Jones, W. R. Refraction and reflection of surface acoustic waves at boundaries of layered anisotropic substrates: gold on lithium niobate. Journal of Applied Physics 1971, 42, 3025-3034.

[16] Tanner, N. A.; Wait, J. R.; Farrar, C. R.; Sohn, H. Structural health monitoring using modular wireless sensors. Journal of Intelligent Material Systems and Structures 2003, 14, 43-56.

[17] Milanese, A.; Marzocca, P.; Nichols, J. M.; Seaver, M.; Trickey, S. T. Modeling and detection of joint loosening using output-only broad-band vibration data. Structural Health Monitoring 2008, 7, 309-328.

[18] Esmaeel, R. A.; Briand, J.; Taheri. F. Computational simulation and experimental verification of a new vibration-based structural health monitoring approach using piezoelectric sensors. Structural Health Monitoring 2011.

[19] Amerini, F.; Meo, M. Structural health monitoring of bolted joints using linear and nonlinear acoustic/ultrasound methods. Structural Health Monitoring 2011.

[20] Kim, N.; Hong, M. Measurement of axial stress using mode-converted ultrasound. NDT & amp; E International 2009, 42, 164-169.

[21] Mascarenas, D. L.; Park, G.; Farinholt, K. M.; Todd, M. D.; Farrar, C. R. A low-power wireless sensing device for remote inspection of bolted joints. *Proceedings of the Institution of Mechanical Engineers, Part G: Journal of Aerospace Engineering* 2009, 223, 565-575.

[22] François, A.; Boehm, J.; Oh, S. Y.; Kok, T.; Monro, T. M. Collection mode surface plasmon fibre sensors: A new biosensing platform. *Biosensors and Bioelectronics* 2011, 26, 3154-3159.

[23] Ballantine, D. S. *Acoustic wave sensors: theory, design, and physico-chemical applications*; Academic Press: San Diego, 1997; p. 436.

[24] Kendall, K.; Tabor, D. An ultrasonic study of the area of contact between stationary and sliding surfaces. *Proceedings of the Royal Society of London. A. Mathematical and Physical Sciences* 1971, 323, 321-340.

[25] Pau, M. Estimation of real contact area in a wheel-rail system by means of ultrasonic waves. *Tribology International* 2003, 36, 687-690.

[26] Królikowski, J.; Szczepek, J. Prediction of contact parameters using ultrasonic method. *Wear* 1991, 148, 181-195.

[27] Drinkwater, B. W.; Dwyer-Joyce. R. S.; Cawley, P. A Study of the interaction between ultrasound and a partially contacting solid-solid interface. *Proceedings of the Royal Society of London. Series A: Mathematical, Physical and Engineering Sciences* 1996, 452, 2613-2628.

[28] Królikowski, J.; Szczepek, J. Phase shift of the reflection coefficient of ultrasonic waves in the study of the contact interface. *Wear* 1992, 157, 51-64.

[29] Takeuchi, A. Establishment of lubrication diagnostic technique with ultrasonic method. *Journal of Japanese Society of Tribologists* 2004, 49, 422-427.

[30] Fischer-Cripps, A. C. *Surfaces forces, adhesion and friction*; Springer-Verlag New York, Inc.: New York, 2000.

[31] Auld, B. A. *Acoustic Fields and Waves in Solids* 2nd ed.; Krieger Pub. Co.: Malabar, Fla., 1990.

[32] Karaman, M.; Atalar, A.; Koymen. H. Optimization of dynamic receive focusing in ultrasound imaging. *Acoustical Imaging* 1992, 19, 225-229.

[33] Collins, J. A.; Staab, G. H.; Busby, H. R. *Mechanical design of machine elements and machines*; John Wiley & Sons: 2002.

[34] Szabo, T. L. *Diagnostic ultrasound imaging: inside out*; Elsevier Academic Press: Amsterdam; Boston, 2004; xxii, p. 549.

[35] Hoskins, P. R.; Martin, K.; Thrush, A. *Diagnostic ultrasound: physics and equipment*, 2nd ed.; Cambridge University Press: Cambridge, UK; New York, 2010; p. 263.

[36] J. Bickford, "Basic concepts," in *Introduction to the design and behavior of bolted joints: non-gasketed joints*, Boca Raton, CRC Press, 2008, pp. 1-8.

[37] V. Giurgiutiu. "Wave propagation SHM with PWAS," in *Structural health monitoring with piezoelectric wafer active sensors*, Burlington, Elsevier Inc., 2008, pp. 435-501.

[38] L. Quifeng, L. Yin, Z. Min, W. Qiong and D. Aimin, "Study on improving time-domain resolution on detecting concrete structures," in *International Conference on Measuring Technology and Mechatronics Automation*, Shanghai, 2011.

[39] V. Giurgiutiu, "Introduction to structural health monitoring," in *Structural health monitoring with piezoelectric wafer active sensors*, Burlington, Elsevier Inc., 2008, pp. 1-10.

[40] X. Zhu, P. Rizzo, A. Marzani and J. Bruck, "Ultrasonic guided waves for nondestructive evaluation/structural health monitoring of trusses," *Measurement science and technology*, no. 21, pp. 1-12, 2010.

[41] J.-R. Lee, J. Takatsubo, N. Toyama and D.-H. Kang, "Health monitoring of complex curved structures using an ultrasonic wavefield propagation imaging system," *Measurement science and technology*, no. 18, pp. 1-10, 2007.

[42] G. Park and D. J. Inman, "Structural health monitoring using piezoelectric impedance measurements," *Philosophical Transaction of the Royal Society* no. 365, pp. 373-392, 2007.

[43] P. Seunghee, L. Jong-Jae, Y. Chung-Bang and D. J. Inman, "Electro-mechanical impedance-based wireless structural health monitoring using PCA-data compression and k-means clustering algorithms," *Journal of Intelligent Materials Systenms and Structures*, vol. 19, pp. 509-520, 2008.

[44] V. Giurgiutiu, "High-frequency vibration SHM with PWAS modal sensors—the electromechanical impedance method," in *Structural health monitoring with piezoelectric wafer active sensors*, Burlington, Elsevier Inc., 2008, pp. 363-433.

[45] S. Bhalla and C. K. Soh, "Structural impedance-based damage diagnosis by piezo-transducer," *Journal of Earthquake Engineering*, no. 32, pp. 1897-1916, 2003.

[46] C. Liang, F. P. Sun and C. A. Rogers, "Coupled electromechanical analysis of adaptative material systems-determination of the actuator power consumption and system energy," *Journal of Intelligent Material and Structures*, no. 5, pp. 12-20, 1994.

[47] S. Lyer, S. K. Sinha, M. k. Pedrick and B. R. Tittman, "Evaluation of ultrasonic inspection and imaging systems for concrete pipes," *Automation in construction*, 2011.

[48] J. Zhu and J. S. Popovics, "Imaging Concrete structures using air-coupled impact-echo," *Journal of engineering mechanics ASCE*. vol. 133, no. 3, 2007.

[49] B. W. Drinkwater and P. D. Wilcox, "Ultrasonic arrays for non-destructive evaluation: a review," *NDT&E International*, no. 39, pp. 525-541, 2006.

[50] Automation Creations, "Matweb," [Online]. Available: http://www.matweb.com/search!DataSheet.aspx?MatGUID=3a9cc570fbb24d 119f08db2 2a53e2421&ckck=1. [Accessed 02 2012].

[51] A. Sisman, "Solid-state arrays and beamformers for side-looking intravascular ultrasonic imaging," Işı k University, Istanbul, Turkey, 2010.

[52] M. Vogt, J. Opretzka and H. Ermet, "Synthetic aperture focusing technique for high-resolution imaging of surface structures with high-frequency ultrasound," in *International Ultrasonics Symposium Proceedings*, Rome, 2009.

[53] M. Schickert, M. Krause and W. Muller, "Ultrasonic imaging of concrete elements using reconstruction by synthetic aperture technique," *Materials in Civil Engineering*, vol. 15, no. 3, 2003.

[54] E. G. Bazulin, "Obtaining flaw images that take the effect of multiple ultrasonic pulse reflections from the boundaries of a test object into account," *Russian Journal of Nondestructive Testing*, vol. 46, no. 10, pp. 735-753, 2010.

[55] M. Spies and H. Rieder, "Synthetic aperture focusing of ultrasonic inspection data to enhance the probability of detection of defects in strongly attenuating materials," *NDT&E International*, no. 43, pp. 425-431, 2010.

[56] L. Quifeng, J. Xinhong, Z. Min, S. Lihua and S. Zhixue, "Simulation on improving resolution of SAFT," in *International Conference on Measuring Technology and Mechatronics Automation*, Zhangjiajie, China, 2009.

V. Giurgiutiu, "Elastic waves in solids and structures," in *Structural health monitoring with piezoelectric wafer active sensors*, Burlington, Elsevier Inc., 2008, pp. 129-182.

J. L. Rose, "Dispersion principles," in *Ultrasonic waves in solid media*, New York, Cambridge University Press, 1999, pp. 5-21.

T. L. Szabo, "Overview," in *Diagnostic ultrasound imaging*, Burlington, Elsevier Inc., 2004, pp. 29-45.

Iowa State University, "NDT Resource center," 2011. [Online]. Available: http://www.ndt-ed.org/EducationResources/CommunityCollege/Ultrasoni cs. [Accessed 02 2012].

J. L. Rose, "Unbounded isotropic and anisotropic media," in *Ultrasonic waves in solid media*, New York, Cambridge University Press, 1999. pp. 24-37.

H. Uberall, "Surface waves in acoustics," in *Physical acoustics principles and methods*, vol. X, New York, Academic Press, Inc., 1973, pp. 1-57.

J. L. Rose, "Surface and subsurface waves," in *Ultrasonic waves in solid media*, New York, Cambridge University Press, 1999, pp. 90-99.

J. D. N. Cheeke, "Rayleigh waves," in *Fundamentals and applications of ultrasonic waves*, Boca Raton, CRC, 2002, pp. 171-186.

T. L. Szabo, "Beamforming," in *Diagnostic ultrasound imaging*, Buslington, Elsevier Inc., 2004, pp. 137-168.

J. L. Rose, "Ultrasonic nondestructive testing principles, analysis and display technology," in *Ultrasonic Waves in solid media*, New York, Cambridge University Press, 1999, pp. 335-357.

K. L. Johnson, "Rough Surfaces," in *Contact mechanics*, New York, N.Y.: Cambridge University Press, 1985, pp. 397-423.

J. Bickford, "Materials," in *Design and behavior of bolted joints: non-gasketed joints*, Boca Raton, CRC Press, 2008, pp. 11-35.

J. Bickford, "Self-Loosening," in *Introduction to design and behavior of bolted joints: non-gasketed joints*, Boca Raton, CRC Press, 2008, pp. 303-325.

J. N. Goodier, "Loosening by vibration of threaded fastenings," *Mechanical Engineering*, no. 67, pp. 798-802, 1945.

J. Bickford, "Torque control of preload," in *Introduction to the design and behavior of bolted joints: non-gasketed joints*, Boca Raton, Fla.: CRC Press, 2008, pp. 137-169.

J. Bickford, "Torque and turn control," in *Introduction to the design and behavior of bolted joints: non-gasketed joints*. Boca Raton, Fla.: CRC Press, 2008, pp. 173-194.

J. Bickford, "Other ways to control Preload," in *Introduction to the design and behavior of bolted joints: non-gasketed joints*, Boca Raton, Fla.: CRC Press, 2008, pp. 197-216.

K. R. Mobley, "Vibration monitoring and analysis," in *An introduction to predictive maintenance*, Woburn, Elsevier Science, 2002, pp. 114-171.

V. Giurgiutiu, "In-situ phased arrays with piezoelectric wafer active sensors," in *Structural health monitoring with piezoelectric wafer active sensors*, Burlington, Elsevier Inc., 2008, pp. 503-587.

C. Tekes, "Ring Array Processing for Forward-Looking Intravascular and Intracardiac Ultrasonic Imaging," Işı k University, Istanbul, Turkey, 2010.

T. L. Szabo, "Array beamforming," in *Diagnostic ultrasound imaging*, Burlington, Elsevier Inc., 2004, pp. 171-209.

G. Gunarathne, "Real-time ultrasonic imaging and advancements in non-conventional methods," in *International Instrumentation and Measurement Technology Conference*, Vancouver, 2008.

T. L. Szabo, "Attenuation," in *Diagnostic Ultrasound Imaging: Inside out*, Burlington, Mass.: Elsevier Inc., 2004, pp. 71-95.

A. Mahmoud, H. Ammar, O. Mukdadi, 1. Ray, F. Imani, A. Chen and J. Davalos, "Non-destructive ultrasonic evaluation of CFRO-concrete specimens subjected to accelerated aging conditions," *NDT&E International*, vol. 43, pp. 635-641, 2010.

V. Giurgiutiu, "Guided Waves," in *Structural health monitoring with piezoelectric wafer active sensors*, Burlington, Mass.: Elsevier Inc., 2008, pp. 185-238.

N. Portzgen, D. Gisolf and D. J. Verschuur, "Wave equation-based imaging of mode converted waves in ultrasonic NDI, with suppressed leakage from nonmode converted waves," *Transactions on Ultrasonics, Ferroelectrics and Frequency Control*, vol. 55, no. 8, pp. 1768-1780, 2008.

P. D. Wilcox, H. Caroline and B. W. Drinkwater, "Advanced reflector characterization with ultrasonic phased arrays in NDE applications," *Transactions on Ultrasonics, Ferroelectrics and Frequency Control*, vol. 54, no. 8, pp. 1541-1550, 2007.

Y. Pio-Liang and L. Pei-Ling, "Imaging of internal cracks in concrete structures using surface rendering technique," *NDT&E International*, vol. 42, pp. 181-187, 2009.

C. Holmes, B. W. Drinkwater and P. D. Wilcox, "Advanced post-processing for scanned ultrasonic arrays: application to defect detection and classification in non-destructive evaluation." *Ultrasonics*, vol. 48, pp. 636-642, 2008.

J. Zhang, B. W. Drinkwater, P. D. Wilcox and A. J. Hunter, "Defect detection using ultrasonic arrays: the multi-mode total focusing method," *NDT&E International*, vol. 43, pp. 123-133, 2010.

T. E. Michaels, J. E. Michaels and M. Ruzzene, "Frequency-wavenumber domain analysis of guided wavefields," *Ultrasonics*, vol. 51, pp. 452-466, 2011.

F. G. Mitri, J. F. Greenleaf and M. Fatemi, "Comparison of continuous-wave (CW) and tone-burst (TB) excitation modes in vibro-acoustography: application for non-destructive imaging of flaws," *Applied Acoustics*, vol. 70, pp. 333-336, 2009.

J. Yiang and I. C. Ume, "Thermomechanical reliability study of flip-chip solder bumps: using laser ultrasound technique and finite element methods," in *Electronic Components and Technology Conference*, 2008.

C. Silva, B. Rocha and A. Suleman, "A structural health monitoring approach based on a PZT network using a tuned wave propagation method," in *Structures, Structural Dynamics and Materials Conference*, Palm Springs, 2009.

V. Giurgiutiu, A. Zagrai and J. Bao, "Embedded active sensors for in-situ structural health monitoring of thin-wall structures," *Journal of Pressure Vessel Technology*, vol. 124, pp. 293-302, 2002.

D. G. Aggelis, T. Shiotani and M. Terazawa, "Assessment of construction joint effect in full-scale concrete beams by acoustic emission activity," *Journal of Engineering Mechanics*, pp. 906-912, 2010.

A. A. Shah and S. Hirose, "Nonlinear ultrasonic investigation of concrete damaged under uniaxial compression step loading," *Journal of Materials in Civil Engineering*, pp. 476-484, 2010.

M. Meo, U. Polimeo and G. Zumpano, "Detecting damage in composite material using nonlinear elastic wave spectroscopy methods," *Applied Composite Materials*, vol. 15, pp. 115-126, 2008.

A. Ledeczi, P. Volgyesi, E. Barth, A. Nadas, A. Pedchenko, T. Hay and S. Jayaraman, "Self-sustaining wireless acoustic emission sensors system for bridge monitoring," Springer-Verlag, Berlin, 2011.

S. Chaki and G. Bourse, "Guided ultrasonic waves for non-destructive monitoring of the stress levels in prestressed steel strands," *Ultrasonics*, vol. 49, pp. 162-171, 2009.

J. Yu, P. Ziehl, B. Zarate and J. Caicedo, "Prediction of fatigue crack growth in steel bridge components using acoustic emission." *Journal of Constructional Steel Research*, no. 67, pp. 1254-1260, 2011.

L. Satyamarayan, J. Chandrasekaran, B. Maxfield and K. Balasubramaniam, "Circumferential higher order guided wave modes for the detection and sizing of cracks and pinholes in pipe support regions," *NDT&E International*, no. 41, pp. 32-43, 2008.

I. Bartoli, S. Salamone, R. Phillips, F. Lanza di Scalea and C. S. Sikorsky, "Use of interwire ultrasonic leakage to quantify loss of prestress in multiwire tendons," *Journal of Engineering Mechanics*, pp. 324-333, 2011.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

GLOSSARY OF CLAIM TERMS

Acoustic beam: This term is used herein to refer to a signal transmitted across a surface to a target (e.g., a bolted joint).

Beamformer: This term is used herein to refer to an apparatus for the transmission, reception, and processing of acoustic waves and signals.

Bolt boundary: This term is used herein to refer to the perimeter of the joint where the outermost real area of contact is located (i.e., the points of contact between the peaks of the joint members that are furthest from the center of the joint or closest to the transducer array).

Distance: This term is used herein to refer to the length or amount of space between a bolt boundary the transducer array element, as determined by the signal reflecting off of said bolt boundary and received by said array element.

Focus point: This term is used herein to refer to an acoustic beam having a resultant pattern ending in a point concentrated on a particular target such as a bolt.

Image: This term is used herein to refer to a representation of the bolt boundary in relation to the transducer array as measured by the distance between the bolt boundary and the transducer array. For example, an image can be an ultrasonic image that indicates the reflection of an acoustic wave off of the bolt boundary of a bolted joint.

Inverse relationship: This term is used herein to refer to a relationship between two properties in which an increase in the value of one property decreases the value of the other property, and vice versa. Thus, if bolt tension and the distance measured between a bolt boundary and a transducer array have an inverse relationship, an increase in distance would equate to a decrease in bolt tension. Conversely, a decrease in distance would equate to an increase in bolt tension.

Joint: This term is used herein to refer to a fastener that joins parts together via the mating of screw heads. A joint can include any parts that would make up the fastener. Examples include, but are not limited to, a bolt, a washer, a nut, the underlying surface, a clamp, etc.

Location of reflection: This term is used herein to refer to the point or area of contact along the bolt boundary at which the acoustic waves fired by the transducer array are reflected. Typically, as tension increases, the location of reflection expands closer to the perimeter of the bolted joint.

Optimal: This term is used herein to refer to the most favorable level of tension in a bolted joint, typically such that the tension is not excessively low or excessively high.

Proper time delay: This term is used herein to refer to an interval of time that represent changes in position of an acoustic wall during reflection. This delay can be adjusted for, in order to determine an accurate time of flight of the reflected acoustic signal.

Real area of contact: This term is used herein to refer to the sum of areas of individual micro-scaled surfaces in contact with each other between the joint members. As tension is increased, the real area of contact spreads toward the perimeter of the joint. The outermost portion of the real area of contact form the bolt boundary that is capable of reflecting surface acoustic waves.

Saturation point: This term is used herein to refer to maximum real area of contact between the peaks of a bolt/washer/joint and the peaks of the underlying surface without being excessively high to cause damage to the underlying surface. This saturation point can be described as the point beyond which increased tension produces only slight changes in bolt boundary position. Prior to the saturation point, there typically are larger changes in bolt boundary position with increasing tension.

Tension: This term is used herein to refer to the preload placed on a bolt to determine the clamping force, which is the force that holds the elements of the joint together. An optimal tension level provides a healthier and safer joint. A joint with excessively low tension tends to lead to loosening of the bolt, and a joint with excessively high tension tends to lead to structural damage of the underlying surface.

Time of flight: This term is used herein to refer to the amount of time that it takes for an acoustic wave to travel a distance through a medium.

Toward: This term is used herein to refer to the general direction of a target, such as a bolt or joint. Thus, when an acoustic beam is direct toward a joint, the acoustic beam is aimed directly at or near said joint, where the acoustic beam (or portions thereof) are capable of reflecting off of the bolt boundary of that joint.

Transducer array: This term is used herein to refer to a group of active elements and crystals that are arranged on the surface of the transducer to fire and receive acoustic waves.

Wedge: This term is used herein to refer to an apparatus that typically includes a transducer for firing and receiving waves/signals.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of measuring or monitoring tension in a bolt threaded into a joint having a bolt boundary formed from a real area of contact between said bolt and an underlying surface, comprising the steps of:
    positioning a transducer array element with a predetermined pitch and at a predetermined distance from said joint;
    generating an acoustic beam formed of surface acoustic waves, said acoustic beam generated by said transducer array element;
    directing said acoustic beam toward said bolt, wherein said surface acoustic waves reflect off of said bolt boundary at said real area of contact, thereby producing a reflected signal,
    said transducer array element receiving said reflected signal;
    determining a distance between said bolt boundary and said transducer array element based on a time of flight of said reflected signal; and
    generating a value of said tension based on said determination of said distance between said bolt boundary and said transducer array element, such that said distance and said value of said tension have an inverse relationship,
    whereby said tension is optimal at a saturation point of said real area of contact between said bolt and said underlying surface.

2. A method of measuring or monitoring tension in a bolt as in claim 1, further comprising:
    said acoustic beam being a variable acoustic beam.

3. A method of measuring or monitoring tension in a bolt as in claim 1, further comprising:
    said transducer array element being a linear array.

4. A method of measuring or monitoring tension in a bolt as in claim 3, further comprising:
    said linear array being a 1-dimensional transducer array.

5. A method of measuring or monitoring tension in a bolt as in claim 1, further comprising:
    said transducer array element being a phased array.

6. A method of measuring or monitoring tension in a bolt as in claim 1, further comprising:
    said transducer array element including a piezoelectric transducer.

7. A method of measuring or monitoring tension in a bolt as in claim 1, further comprising:
    said transducer array element being an aspect of a crystal wedge that directs said acoustic beam toward said bolt.

8. A method of measuring or monitoring tension in a bolt as in claim 1, further comprising:
    said reflected signal processed by a beamformer to generate an image of said bolt boundary, said beamformer connected to said transducer array element.

9. A method of measuring or monitoring tension in a bolt as in claim 8, further comprising the step of:
    applying a proper time delay to said reflected signal to determine said time of flight and a location of reflection of said reflected signal.

10. A method of measuring or monitoring tension in a bolt as in claim 1, further comprising:
    said step of determining said distance between said bolt boundary and said transducer array element performed by generating an ultrasonic image of said joint in order to quantify said real area of contact.

11. A method of measuring or monitoring tension in a bolt as in claim 1, further comprising:
    said transducer array element further generating a plurality of acoustic beams from a plurality of predefined positions to produce an array of reflected signals used to determine said distance between said bolt boundary and said transducer array element.

12. A method of measuring or monitoring tension in a bolt as in claim 11, further comprising:
    said array of reflected signals arranged and used to construct one (1) acoustic image of said bolt boundary.

13. A method of measuring or monitoring tension in a bolt as in claim 1, further comprising:
    said transducer array element having a focus point at said bolt.

14. A method of measuring or monitoring tension in a bolt threaded into a joint having a bolt boundary formed from a real area of contact between said bolt and an underlying surface, comprising the steps of:
    positioning a crystal wedge at a predetermined distance from said joint, said crystal wedge including a 1-dimensional, linear phased transducer array with a predetermined pitch, said transducer array including a piezoelectric transducer,
    generating a plurality of variable acoustic beams formed of surface acoustic waves, said plurality of acoustic beams generated by said transducer array from a plurality of predefined positions;
    directing said plurality of acoustic beams toward said bolt, wherein said surface acoustic waves reflect off of said bolt boundary at said real area of contact, thereby producing an array of reflected signals,
    said transducer array receiving said array of reflected signals;
    determining a distance between said bolt boundary and said transducer array based on a time of flight of said array of reflected signals,
    said time of flight of said array of reflected signals generated by applying a proper time delay to said array of reflected signals, said application of said proper time delay further generating locations of reflection of said array of reflected signals,
    said distance determined by a beamformer connected to said transducer array and processing said array of reflected signals to generate an ultrasonic image of said joint and said bolt boundary in order to quantify said real area of contact; and
    generating a value of said tension based on said determination of said distance between said bolt boundary and said transducer array, such that said distance and said value of said tension have an inverse relationship,
    whereby said tension is optimal at a saturation point of said real area of contact between said bolt and said underlying surface.

15. A system for measuring or monitoring tension in a bolt threaded into a joint having a bolt boundary formed from a real area of contact between said bolt and an underlying surface, comprising:
    a transducer array with a predetermined pitch positioned at a predetermined distance from said joint, said transducer array generating and directing an acoustic beam toward said bolt, said acoustic beam formed of surface acoustic waves that reflect off of said bolt boundary at said real area of contact, thereby producing a reflected signal that is received by said transducer array; and
    a beamformer connected to said transducer array and generating an acoustic image of said joint, thereby permitting a determination of a distance between said bolt boundary and said transducer array,
wherein said distance and said tension have an inverse relationship, whereby said tension is optimal at a saturation point of said real area of contact between said bolt and said underlying surface.

\* \* \* \* \*